(12) United States Patent
Malafa et al.

(10) Patent No.: US 8,846,653 B2
(45) Date of Patent: Sep. 30, 2014

(54) DELTA-TOCOTRIENOL TREATMENT AND PREVENTION OF PANCREATIC CANCER

(71) Applicant: University of South Florida, Tampa, FL (US)

(72) Inventors: Mokenge P. Malafa, Tampa, FL (US); Said M. Sebti, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 13/653,108

(22) Filed: Oct. 16, 2012

(65) Prior Publication Data

US 2014/0235659 A1    Aug. 21, 2014

Related U.S. Application Data

(63) Continuation-in-part of application No. 11/768,373, filed on Jun. 26, 2007, now Pat. No. 8,288,369.

(60) Provisional application No. 60/805,916, filed on Jun. 27, 2006.

(51) Int. Cl.
| | |
|---|---|
| *A61K 31/355* | (2006.01) |
| *A61K 31/513* | (2006.01) |
| *A61K 31/7052* | (2006.01) |
| *A61K 31/7105* | (2006.01) |
| *A61P 35/00* | (2006.01) |

(52) U.S. Cl.
USPC ............ 514/183; 514/274; 514/458; 435/374

(58) Field of Classification Search
None
See application file for complete search history.

(56) References Cited

PUBLICATIONS

Hidalgo et al. Phase I-II study of gemcitabine and fluorouracil as a continuous infusion in patients with pancreatic cancer. Journal of Clinical Oncology, vol. 17, No. 2. Feb. 1999, pp. 585-592.*
Ting-Chao Chou, Drug Combination Studies and Their Synergy Quantification Using the Chou-Talalay Method. Cancer Research, vol. 70, No. 2, Jan. 12, 2010. pp. 440-446.
Chuangui Wang, Xinghua Hou, Subhra Mohapatra, Yihong Ma, W. Douglas Cress, W. Jack Pledger, and Jiandong Chen, Activation of p27kip1 Expression by E2F1. vol. 280, No. 13. Issue of Apr. 1, 2005. pp. 12339-12343.
Greer et al., Julia B. "Genetic Predisposition to Pancreatic Cancer: A Brief Review." American Journal of Gastroenterology, 2007. ISSN 0002-9270. pp. 2564-2569.
Chou et al., Ting-Chao. "Computerized Quantitation of Synergism and Antagonism of Taxol, Topotecan, and Cisplatin Against Human Teratocarcinoma Cell Growth: A Rational Approach to Clinical Protocol Design." Journal of the National Cancer Institute, vol. 86, No. 20, Oct. 1994. Reports 1517-1524.

* cited by examiner

*Primary Examiner* — Anna Pagonakis
(74) *Attorney, Agent, or Firm* — Robert J. Varkonyi; Smith & Hopen, P.A.

(57) ABSTRACT

Methods are disclosed for treating neoplastic disorders, such as pancreatic cancer, using tocotrienols; namely, gamma-tocotrienol and delta tocotrienol. The antitumorogenic effects of these compounds are shown both in vitro and in vivo using several human pancreatic cancer cell lines and MIA-PACA2 human pancreatic cancer cells xenografted in nude mice. Also disclosed are methods of testing the efficacy of potential chemotherapeutic agents by measuring their effect on surrogate endpoint biomarkers, such as Ki-67 and p27. Associated compounds are also disclosed.

14 Claims, 39 Drawing Sheets

|  | 24h | 48h |
|---|---|---|
| Control | 100 | 100 |
| Vehicle | 101 | 102 |
| alpha T3 | 121 | 116 |
| beta T3 | 99 | 68 |
| gamma T3 | 107 | 89 |
| delta T3 | 97 | 83 |
| alpha T | 122 | 107 |
| gamma T | 116 | 94 |
| TS | 110 | 104 |
| GG | 92 | 83 |
| SA | 109 | 105 |

|        | 24h | 48h |
|--------|-----|-----|
| Control | 100 | 100 |
| Vehicle | 95 | 101 |
| alpha T3 | 116 | 93 |
| beta T3 | 79 | 61 |
| gamma T3 | 66 | 37 |
| delta T3 | 77 | 67 |
| alpha T | 111 | 86 |
| gamma T | 121 | 81 |
| TS | 96 | 76 |
| GG | 82 | 53 |
| SA | 105 | 90 |

Vehicle         100 MPK

V = viable tumor

N = Area of tumor necrosis

% = percent positive staining

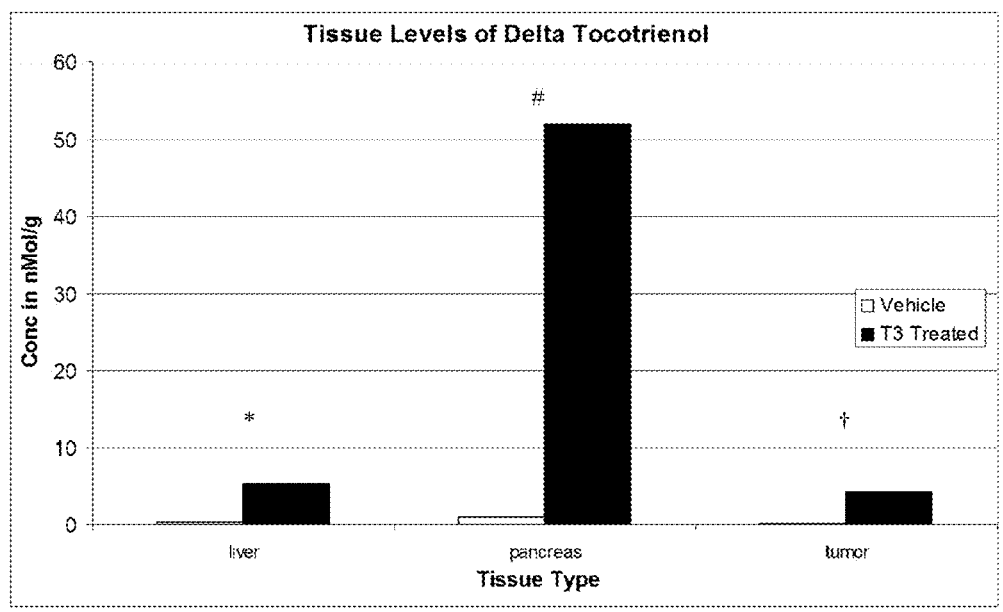

DELTA-TOCOTRIENOL TREATMENT AND PREVENTION OF PANCREATIC CANCER

CROSS REFERENCE TO RELATED APPLICATIONS

This application is a continuation-in-part application of U.S. application Ser. No. 11/768,373, entitled "Delta-Tocotrienol Treatment and Prevention of Pancreatic Cancer," filed on Jun. 26, 2007; which claims priority to U.S. Provisional Application, No. 60/805,916, entitled "δ-Tocotrienol Treatment of Pancreatic Cancer," filed on Jun. 27, 2006; which are fully incorporated herein by reference.

STATEMENT OF GOVERNMENT INTEREST

This invention was made with Government support under Grant No. DAMD 17-01-1-04 awarded by the Department of Defense, and NCI Grant No. 3R01CA098473-03S1. The Government has certain rights in the invention.

BACKGROUND OF THE INVENTION

The pancreas is an extremely common site for the development of early neoplasms-noninvasive clonal epithelial expansions. In a minority of persons, these clones of cells serially acquire genetic changes that can lead to an invasive adenocarcinoma. Pancreatic cancer, once invasive, is almost uniformly fatal. The epithelial cells in the advanced stage of this process are very aggressive, seemingly having an innate capability for metastasis that is exhibited rather soon after they invade beyond the duct structure into surrounding tissue. In order to alleviate the dismal prognosis associated with this disease, it is imperative that the process of pancreatic carcinogenesis be recognized and treated prior to invasion. Chemoprevention is the administration of agents (drugs, biologics, and nutrients) to slow progression of, reverse, or inhibit carcinogenesis thereby lowering the risk of developing invasive or clinically significant disease. Understanding the morphology and biology of precursor lesions of invasive pancreatic cancer has therefore become an issue of paramount importance. In the last decade, significant progress has been made in the recognition and appropriate classification of these precursor lesions. Mucinous cystic neoplasms (MCNs), intraductal papillary mucinous neoplasms (IPMNs), and pancreatic intraepithelial neoplasia (PanIN) encompass the three known morphologically distinct precursors to invasive pancreatic cancer.

A large number of case-control and cohort studies have shown that there is a significant clustering of pancreatic cancer in some families. These high-risk inherited pancreatic cancers are estimated to represent about 10% of pancreatic cancers. Five well-known genetic syndromes with known gene defects account for approximately 20% of the families in which there is aggregation of pancreatic cancer. These syndromes include (1) BRCA2, (2) familial atypical multiple mole melanoma (p16/CDKN2A), (3) Peutz-Jeghers Syndrome; (4) HNPCC; and (5) familial pancreatitis. Majority of pancreatic cancers are sporadic and have evidence of widespread chromosomal instability, including a high rate of translocations and deletions. Nearly all (>90%) preinvasive lesions have an early mutation in the K-Ras protein involved in the transmission of growth factor signals. In the middle stages of preinvasive progression >90% of lesions develop inactivation of the CDKN2A (p16) cyclin dependent kinase inhibitor. In later stages most preinvasive lesions also harbor mutations of the TP53 (p53) and in MADH4, the common Smad protein involved in transduction of TGFβ and activin signals. Despite the enormous obvious benefit for chemopreventive agents in pancreatic neoplasia, direct drug investigations for chemopreventive indications have been slow to emerge. A critical factor is the challenge of conducting studies that will define and demonstrate clinical benefit.

Proliferation of pancreatic cancer is regulated through aberrant oncogenic Ras signaling and its effect on cyclin kinase inhibitors such as $p27^{kip1}$. Previous studies have demonstrated that pharmacologic inhibition of one of the ras signaling pathways, the Raf-MEK-ERK pathway, elicits pancreatic cancer cell cycle arrest through induced expression of p27 (Cancer Res 2005; 65(11):4870-80). Tocotrienols, the chemical form of vitamin E with an unsaturated isoprenoid side chain, are receiving attention as promising dietary supplements for cancer prevention and treatment.

Tocotrienols are the primary form of vitamin E in the seeds of most monocot plants such as palm and cereals such as rice and wheat. The biosynthesis of tocotrienols and tocopherols occur exclusively in photosynthetic organisms and arise from homogentisic acid. Tocotrienols arise from the condensation of homogentisic acid and geranylgeranyl diphosphate while the committed step in tocopherol synthesis is the condensation of homogentisic acid and phytyl diphosphate. Structurally tocopherols and tocotrienols share some resemblance consisting of a common chromanol head and a side chain at the C-2 position however, their side chains distinguish tocopherols and tocotrienols.

While tocopherol has a saturated phytyl tail, tocotrienol possesses an unsaturated isoprenoid side chain. Tocopherols and tocotrienols are further separated into individual compounds assigned by the greek letter prefixes ($\alpha$, $\beta$, $\gamma$, $\delta$) depending on the number and position of methyl substitution on the chromanol ring. As reflected in their structural similarity, tocopherols and tocotrienols are well recognized for their antioxidant effect. However, tocotrienols are the group of natural vitamin E compounds with clear and consistent antitumor activity. Semisynthetic tocopherols such as tocopherol succinate have antitumor activity however the bioavailability of the intact compound after oral consumption is poor making it unsuitable for chemopreventive interventions. Structure activity studies of the proapoptotic effects of vitamin E compounds have clearly documented the importance of the unsaturated isoprenoid tail of the vitamin E compounds in their antitumor bioactivity. Furthermore, these studies indicate that decreasing the number of methyl substitutions on the chromanol ring, is associated with increasing antitumor potency.

SUMMARY OF INVENTION

In one embodiment, the invention includes a method of determining the effectiveness of a chemotherapeutic agent by determining, in an isolated sample, a first level of a surrogate endpoint biomarker such as p27. The sample is then contacted with an experimentally effective amount of the chemotherapeutic agent being tested. After the chemotherapeutic agent has been administered, a second level of the surrogate endpoint biomarker is taken and compared to the first (pre-treatment) level. The candidate chemotherapeutic agent demonstrates effectiveness where the second (post-treatment) level of p27 is increased to a statistically significant degree over the pre-treatment and/or control levels.

In another embodiment, the invention provides a method of determining the effectiveness of a chemotherapeutic agent by further determining, in the isolated sample, a first level of a second surrogate endpoint biomarker such as Ki-67 and/or p-MAPK. After the chemotherapeutic agent has been administered, a second level of Ki-67 and/or p-MAPK is taken and compared to the first (pre-treatment) level and/or a control. The candidate chemotherapeutic agent demonstrates effectiveness where the second (post-treatment) level of Ki-67 and/or p-MAPK is decreased to a statistically significant degree below the pre-treatment and/or control levels.

Another embodiment of the invention includes a method of screening for pancreatic ductal carcinoma, or a stage of pancreatic cancer in a subject by determining, such as in an isolated sample, the level of a biomarker; namely, p27. The level of the biomarker is then compared to a corresponding control level in one or more control samples. In a preferred embodiment the control samples are obtained from individuals who have been determined not to have pancreatic ductal carcinoma, or a stage of pancreatic cancer.

The determination of a statistically significant similarity between the level of the biomarker in the subject and the level of the biomarker in the control sample(s) is indicative of the lack of pancreatic ductal carcinoma, or a stage of pancreatic cancer in the subject. A statistically significant decrease in the level of p27 in the subject, compared to the level of the biomarker in the control sample(s), indicates the presence of pancreatic ductal carcinoma, or a stage of pancreatic cancer in the subject.

In an alternate embodiment, the level of a second biomarker, namely Ki-67 and/or p-MAPK, is determined and compared to a control level of Ki-67 and/or p-MAPK in one or more control samples. A statistically significant increase between the level of Ki-67 and/or p-MAPK in the subject and the control sample(s) is indicative of pancreatic ductal carcinoma, or a stage of pancreatic cancer in the subject. A statistically significant similarity in the level of Ki-67 and/or p-MAPK in the subject, compared to the control sample(s), is indicative of the lack of pancreatic ductal carcinoma, or a stage of pancreatic cancer in the subject.

Methods of determining the level of the biomarker in the subject and control sample(s) are known to the ordinary practitioner. In one embodiment, as an example, the level of the biomarker is determined utilizing an antibody which binds the biomarker. The sample containing the biomarker is contacted with the antibody under conditions which allow binding of the biomarker to the antibody; the presence of the biomarker can then be quantified.

The invention also includes compositions useful in performing the associated methods. For example, the invention includes a composition comprising a plurality of isolated proteins which bind selectively to the protein products of the associated biomarkers; namely, Ki-67 and/or p-MAPK, and p27. In a preferred embodiment, the isolated proteins selectively amplify complementary double stranded DNA. A composition is also included comprising a plurality of biomarker specific primers, wherein each biomarker specific primer selectively amplifies double stranded DNA complementary to a unique biomarker such as Ki-67, p-MAPK, and p27. Alternatively, the invention includes a composition comprising a plurality of isolated proteins which bind selectively to the protein products of at least two unique biomarkers, wherein each unique biomarker is selected from the group consisting of Ki-67, p-MAPK and p27.

Accordingly, the invention includes method of treating cancer, such as pancreatic ductal carcinoma, or a stage of pancreatic cancer, by administering to a subject a composition comprising a therapeutically effective amount of a tocotrienol. In a preferred embodiment the tocotrienol is gamma-tocotrienol and/or delta-tocotrienol, which is administered as a pharmaceutical composition. The composition of the preferred embodiment is substantially free of alpha-tocotrienol, beta-tocotrienol and/or tocopherols. Although one of ordinary skill will recognize methods of determining the appropriate dose, the composition of one embodiment comprises between about 100 mg and 300 mg tocotrienol which is administered twice daily.

The tocotrienol of the preferred embodiment has the formula:

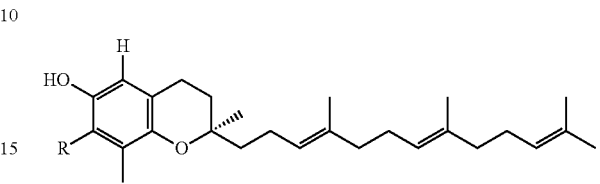

wherein R is selected from the group consisting of H and $CH_3$.

BRIEF DESCRIPTION OF THE DRAWINGS

For a fuller understanding of the nature and objects of the invention, reference should be made to the following detailed description, taken in connection with the accompanying drawings, in which:

FIG. 52 is a graph showing tissue levels of delta-tocotrienol. *p=0.0044; # p=0.0034; † p=0.0181.

DETAILED DESCRIPTION OF THE PREFERRED EMBODIMENT

Figure 1:
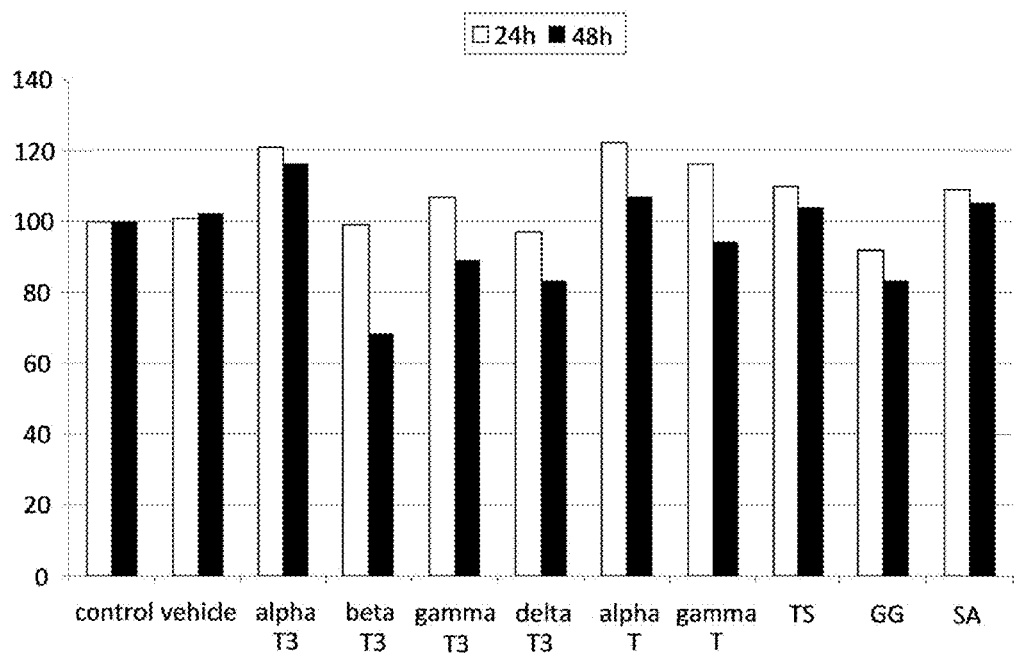
FIG. 1 is a graph of the MTS analysis of SW1990 pancreatic cancer cells (Panc-1), 24 and 48 hours, shown in Tables I-II.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The invention provides a method utilizing δ-tocotrienol and fluorouracil (5-FU) to inhibit pancreatic tumor growth, prevent malignant transformation, and induce apoptosis in vitro. The antitumorigenic properties of δ-tocotrienol in vitro are shown herein using human pancreatic ductal carcinoma cell lines (MIA PaCa2, SW1990, BXPC3) from American type tissue culture (ATTC, Rockville, Md.), which were acquired, grown at 70% confluency per protocol, and treated with δ-tocotrienol. Immortalized human pancreatic ductal epithelial cells, HPDE 6C7, were treated under identical conditions to investigate δ-tocotrienols selective effects on pancreatic cancer cells. Results show that δ-tocotrienol selectively inhibits transformation and proliferation.

As used herein, the term "biomarker" refers to a gene that is differentially expressed in individuals having cancer, including pancreatic cancer or a stage of pancreatic cancer as compared with those not having cancer, including pancreatic or a stage of pancreatic cancer. The term "biomarker" can include a gene that is differentially expressed in individuals having superficial pancreatic cancer as compared with those not having pancreatic cancer.

The term "biomarker specific primers" as used herein refers to a set of primers which can produce double stranded DNA complementary to a portion of one or more RNA products of the biomarker of the invention. For example, the primers can include a first primer which is a sequence that can selectively hybridize to RNA, cDNA or EST complementary to a biomarker of the invention to create an extension product and a second primer capable of selectively hybridizing to the extension product, which are used to produce double stranded DNA complementary to a biomarker of the invention.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art. In general, the design and selection of primers embodied by the instant invention is according to methods that are standard and well known in the art, see Dieffenbach, C. W., Lowe, T. M. J., Dveksler, G. S. (1995) General Concepts for PCR Primer Design. In: PCR Primer, A Laboratory Manual (Eds. Dieffenbach, C. W, and Dveksler, G. S.) Cold Spring Harbor Laboratory Press, New York, 133-155; Innis, M. A., and Gelfand, D. H. (1990) Optimization of PCRs. In: PCR protocols, A Guide to Methods and Applications (Eds. Innis, M. A., Gelfand, D. H., Sninsky, J. J; and White, T. J.) Academic Press, San Diego, 3-12; Sharrocks, A. D. (1994) The design of primers for PCR. In: PCR Technology, Current Innovations (Eds. Griffin, H. G., and Griffin, A. M, Ed.) CRC Press, London, 5-11.

The term "biomarker specific probe" as used herein refers to a probe selectively and specifically hybridizes to RNA products of a unique biomarker. In one embodiment a biomarker specific probe can be a probe having a fluorophore and a quencher, for example a TaqMan® probe or a Molecular Beacons probe. In another embodiment a biomarker specific probe is a probe which is attached to an array and selectively and specifically hybridizes to one or more RNA products (or cDNA, EST or PCR products corresponding to said RNA products) of a unique biomarker. A biomarker specific probe can include oligonucleotide probes and can also include longer probes (e.g. 60, 80, 100, 150, 200, 250, 300, 350, 400, 450, 500 Nucleotides etc.).

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length. Probes can include oligonucleotides modified so as to have a tag which is detectable by fluorescence, chemiluminescence and the like. The probe can also be modified so as to have both a detectable tag and a quencher molecule, for example Taqman® and Molecular Beacon® probes.

As used herein, the term "product of the biomarker" or "biomarker product" refers to the RNA or protein which corresponds or is encoded by the biomarker (i.e. is transcribed from the gene or genetic element or is translated from RNA which is transcribed from the gene or genetic element). For example, in some embodiments RNA resulting from the biomarker can include one or more of the following species; hnRNA, mRNA, and/or one or more spliced variants of mRNA. In some embodiments, proteins resulting from the molecular marker can include any proteins found in blood which correspond to the RNA resulting from the biomarker.

As used herein, the term "control" or "control sample" in the context of this invention refers to one or more tissue nucleic acid samples and/or a blood nucleic acid samples and/or one or more individuals who are classified as having pancreatic cancer, having one or more stages of pancreatic cancer and/or superficial bladder cancer; not having pancreatic cancer, having one or more stages of pancreatic cancer and/or superficial bladder cancer; as determined by using those techniques known to a person skilled in the art. The term control or control sample can also refer to the compilation of data derived from samples of one or more individuals who have been diagnosed as normal (not having pancreatic cancer), having pancreatic cancer, or having a stage of pancreatic cancer. As would be understood by a person skilled in the art—the term control is used in the context of the experiment and will depend upon the desired comparisons. As used herein, the term "control" in the context of screening for a prophylactic or therapeutic agent refers to a standard or reference for an assay or methodology to which other conditions can be compared.

As used herein, the term "effective amount" refers to the amount of a compound which is sufficient to reduce or ameliorate the progression and or severity of pancreatic cancer or one or more symptoms thereof, prevent the development, recurrence or onset of pancreatic cancer or one or more symptoms thereof, prevent the advancement of pancreatic cancer or one or more symptoms thereof, or enhance or improve the prophylactic or therapeutic effect(s) of another therapy.

As used herein, the terms "chemotherapeutic agent" refers to any compound(s) which can be used in the treatment, management or amelioration of pancreatic cancer or one or more symptoms thereof.

As used herein, the term "therapeutically effective amount" refers to that amount of a therapy (e.g., a chemotherapeutic agent) sufficient to result in the amelioration of pancreatic cancer or one or more symptoms thereof, prevent advancement of bladder cancer cause regression of bladder cancer, or to enhance or improve the therapeutic effect(s) of another therapy (e.g., chemotherapeutic agent). As used herein, the term "efficacy" refers to the effectiveness of a drug and/or.

"Chemotherapeutic efficacy" is usually measured by the clinical response of the patient who has been or is being treated with a drug and/or agent. A drug is considered to have a high degree of efficacy, if it achieves desired clinical results, for example, the reduction of the symptoms associated with pancreatic cancer, a stage of pancreatic cancer, or the prevention of pancreatic cancer progression as described in the present specification. The amount of drug absorbed may be used to predict a patient's response. A general rule is that as the dose of a drug is increased, a greater effect is seen in the patient until a maximum desired effect is reached.

As used herein, the term "level of expression" refers to the determination of the quantity of a given nucleic acid or protein corresponding to a gene as determined by methods known to a person skilled. In reference to RNA, hnRNA, mRNA or spliced variants of mRNA corresponding to a biomarker of the invention, level of expression can be determined by hybridization as well as other measurements such as quantitative real-time RT PCR, which includes use of SYBR™ green, TaqMan® and Molecular Beacons technology. Note that as used herein the determination of differential levels of expression can include a visual inspection of differences as between the quantity of a given nucleic acid or protein, for example by analyzing the northern blot or western blot.

As used herein, the term "selectively amplified" or "selective amplification", refers to a process whereby one or more copies of a particular target nucleic acid sequence is selectively generated from a template nucleic acid. Selective amplification or selectively amplified is to be compared with amplification in general which can be used as a method in combination with, for example, random primers and an oligodT primer to amplify a population of nucleic acid sequences (e.g. mRNA). Selective amplification is preferably done by the method of polymerase chain reaction (Mullis and Faloona, 1987, Methods Enzymol. 155:335).

As used herein, the term "selectively binds" in the context of proteins encompassed by the invention refers to the specific interaction of any two of a peptide, a protein, a polypeptide, and an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognizes and binds to a structure on the second molecule, rather than to other proteins. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

Example 1

SW1990 pancreatic cancer cells (Panc-1) were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine. HPDE6-C7 cells were cultured in serum-free keratinocyte SFM media. All cells were maintained at 37° C. in a humidified incubator with 5% $CO_2$. The cells were treated with a single 50 μM dose of vehicle (ethanol extracted olive oil), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). A control culture (i.e., only vehicle with no treatment) was grown alongside the treatments for comparison. Cell viability was measured using MTS assay at preselect times of 24, 48, or 72 hours after treatment. There was minimal effect from the different compositions at 24 hours, as seen by Table 1.

Table 1.

MTS assay results of SW1990 cultures 24 hours after treatment. The MTS assay was run 9 times, with the results from each run shown in the different columns. The final column shows the relative value set to the control of the 9 runs.

| run # | 1 | 2 | 3 | 4 | 5 | 6 | 7 | 8 | 9 | rel amnt |
|---|---|---|---|---|---|---|---|---|---|---|
| Control | 0.167 | 0.156 | 0.151 | 0.161 | 0.142 | 0.147 | 0.142 | 0.109 | 0.147 | 100 |
| Vehicle | 0.15 | 0.146 | 0.147 | 0.14 | 0.155 | 0.151 | 0.164 | 0.138 | 0.149 | 101 |
| T3 alpha | 0.168 | 0.183 | 0.175 | 0.148 | 0.195 | 0.176 | 0.206 | 0.172 | 0.178 | 121 |
| T3 beta | 0.164 | 0.168 | 0.167 | 0.123 | 0.138 | 0.143 | 0.126 | 0.134 | 0.145 | 99 |
| T3 gamma | 0.169 | 0.161 | 0.163 | 0.143 | 0.15 | 0.158 | 0.159 | 0.151 | 0.157 | 107 |
| T3 delta | 0.158 | 0.149 | 0.157 | 0.126 | 0.147 | 0.135 | 0.13 | 0.142 | 0.143 | 97 |
| T alpha | 0.188 | 0.183 | 0.189 | 0.166 | 0.183 | 0.181 | 0.186 | 0.16 | 0.180 | 122 |
| T gamma | 0.175 | 0.165 | 0.167 | 0.154 | 0.198 | 0.168 | 0.178 | 0.16 | 0.171 | 116 |
| TS | 0.155 | 0.168 | 0.164 | 0.158 | 0.155 | 0.163 | 0.165 | 0.167 | 0.162 | 110 |
| GG | 0.158 | 0.133 | 0.133 | 0.137 | 0.131 | 0.14 | 0.132 | 0.121 | 0.136 | 92 |
| SA | 0.146 | 0.154 | 0.15 | 0.152 | 0.172 | 0.165 | 0.179 | 0.165 | 0.160 | 109 |

The tocotrienols, particularly beta and delta, show reduced cell viability by 48 hours, as seen in Table 2. Notably, the gamma- and delta-tocotrienol show comparable or improved anti-proliferative effects as compared to the chemotherapeutic geranylgeraniol.

Table 2.

MTS assay results of SW1990 cultures 48 hours after treatment. The MTS assay was run 9 times, with the results from each run shown in the different columns. The final column shows the relative value set to the control of the 9 runs.

| run # | 1 | 2 | 3 | 4 | 5 | 6 | 7 | 8 | 9 | rel amnt |
|---|---|---|---|---|---|---|---|---|---|---|
| Control | 0.161 | 0.156 | 0.16 | 0.137 | 0.148 | 0.152 | 0.15 | 0.152 | 0.152 | 100 |
| Vehicle | 0.169 | 0.152 | 0.16 | 0.146 | 0.143 | 0.149 | 0.16 | 0.162 | 0.154 | 102 |
| T3 alpha | 0.168 | 0.162 | 0.16 | 0.146 | 0.175 | 0.205 | 0.2 | 0.187 | 0.175 | 116 |

-continued

| run # | 1 | 2 | 3 | 4 | 5 | 6 | 7 | 8 | 9 | rel amnt |
|---|---|---|---|---|---|---|---|---|---|---|
| T3 beta | 0.108 | 0.093 | 0.09 | 0.104 | 0.109 | 0.117 | 0.1 | 0.102 | 0.104 | 68 |
| T3 gamma | 0.114 | 0.125 | 0.13 | 0.123 | 0.137 | 0.137 | 0.16 | 0.16 | 0.135 | 89 |
| T3 delta | 0.131 | 0.133 | 0.12 | 0.12 | 0.126 | 0.119 | 0.12 | 0.142 | 0.127 | 83 |
| T alpha | 0.172 | 0.17 | 0.16 | 0.154 | 0.154 | 0.167 | 0.18 | 0.146 | 0.163 | 107 |
| T gamma | 0.131 | 0.133 | 0.14 | 0.141 | 0.142 | 0.122 | 0.16 | 0.164 | 0.142 | 94 |
| TS | 0.122 | 0.166 | 0.16 | 0.135 | 0.148 | 0.174 | 0.18 | 0.173 | 0.157 | 104 |
| GG | 0.078 | 0.129 | 0.13 | 0.128 | 0.133 | 0.118 | 0.14 | 0.144 | 0.125 | 83 |
| SA | 0.122 | 0.149 | 0.17 | 0.138 | 0.177 | 0.159 | 0.18 | 0.178 | 0.159 | 105 |

By 72 hours after treatment, the gamma- and delta-tocotrienol compositions show enhanced anti-proliferative effect, comparable to both tocopherol succinate and geranylgeraniol, as seen in Table 3. These results are further illustrated in FIG. 1, which represents the results for the 24 hour and 48 hour trials.

Table 3.

MTS assay results of SW1990 cultures 72 hours after treatment. The MTS assay was run 9 times, with the results from each run shown in the different columns. The final column shows the relative value set to the control of the 9 runs.

| run # | 1 | 2 | 3 | 4 | 5 | 6 | 7 | 8 | 9 | rel amnt |
|---|---|---|---|---|---|---|---|---|---|---|
| Control | 0.464 | 0.511 | 0.45 | 0.421 | 0.428 | 0.42 | 0.43 | 0.433 | 0.444 | 100 |
| Vehicle | 0.409 | 0.358 | 0.35 | 0.321 | 0.345 | 0.304 | 0.32 | 0.336 | 0.344 | 77 |
| T3 alpha | 0.279 | 0.282 | 0.29 | 0.238 | 0.302 | 0.279 | 0.25 | 0.254 | 0.273 | 61 |
| T3 beta | 0.349 | 0.316 | 0.33 | 0.298 | 0.323 | 0.287 | 0.28 | 0.275 | 0.307 | 69 |
| T3 gamma | 0.776 | 0.744 | 0.88 | 0.734 | 0.812 | 0.817 | 0.77 | 0.759 | 0.786 | 177 |
| T3 delta | 0.667 | 0.615 | 0.61 | 0.587 | 0.582 | 0.491 | 0.52 | 0.604 | 0.584 | 132 |
| T alpha | 0.523 | 0.478 | 0.46 | 0.453 | 0.443 | 0.456 | 0.38 | 0.451 | 0.456 | 103 |
| T gamma | 0.5 | 0.497 | 0.46 | 0.505 | 0.515 | 0.469 | 0.43 | 0.451 | 0.478 | 108 |
| TS | 0.998 | 0.962 | 1.02 | 0.887 | 0.936 | 0.897 | 0.85 | 0.801 | 0.918 | 207 |
| GG | 0.784 | 0.713 | 0.76 | 0.734 | 0.682 | 0.665 | 0.65 | 0.627 | 0.702 | 158 |
| SA | 0.596 | 0.547 | 0.57 | 0.515 | 0.544 | 0.44 | 0.4 | 0.427 | 0.504 | 113 |

Example 2

BXPC3 cells were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine HPDE6-C7 cells were cultured in serum-free keratinocyte SFM media. All cells were maintained at 37° C. in a humidified incubator with 5% $CO_2$. The cells were treated with a single 50 μM dose of vehicle (vehicle only, may be a solvent), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). A control (no treatment) culture was grown alongside the treatments for comparison. Cell viability was measured using MTT assay at preselect times of 48 or 120 hours after treatment. At 48 hours there is minimal effect from the different compositions, as seen by Table 4.

Table 4.

MTT assay results of BXCPC3 cultures 48 hours after treatment. The MTT assay was run 7 times, with the results from each run shown in the different columns. A blank was also tested. The final column shows the relative value set to the control of the 7 runs (av=average).

| run # | 1 | 2 | 3 | 4 | 5 | 6 | 7 | av | av-blank | rel amt |
|---|---|---|---|---|---|---|---|---|---|---|
| Blank | 0.048 | 0.047 | 0.049 | 0.051 | 0.05 | 0.047 | 0.049 | | | |
| Control | 0.279 | 0.282 | 0.28 | 0.273 | 0.267 | 0.287 | 0.274 | 0.277 | 0.228 | 100 |
| Vehicle | 0.255 | 0.274 | 0.276 | 0.256 | 0.295 | 0.292 | 0.285 | 0.276 | 0.227 | 100 |
| T3 alpha | 0.279 | 0.275 | 0.295 | 0.301 | 0.3 | 0.273 | 0.275 | 0.285 | 0.236 | 104 |
| T3 beta | 0.263 | 0.261 | 0.27 | 0.254 | 0.278 | 0.255 | 0.274 | 0.265 | 0.216 | 95 |
| T3 gamma | 0.259 | 0.257 | 0.289 | 0.279 | 0.268 | 0.292 | 0.283 | 0.275 | 0.226 | 99 |
| T3 delta | 0.26 | 0.255 | 0.24 | 0.263 | 0.271 | 0.288 | 0.265 | 0.216 | | 95 |
| T alpha | 0.333 | 0.328 | 0.352 | 0.296 | 0.3 | 0.341 | 0.312 | 0.323 | 0.274 | 120 |
| T gamma | 0.32 | 0.356 | 0.335 | 0.304 | 0.277 | 0.28 | 0.306 | 0.311 | 0.262 | 115 |
| TS | 0.271 | 0.274 | 0.296 | 0.271 | 0.282 | 0.274 | 0.277 | 0.278 | 0.229 | 100 |
| GG | 0.308 | 0.272 | 0.299 | 0.291 | 0.299 | 0.3 | 0.294 | 0.295 | 0.246 | 108 |
| SA | 0.273 | 0.28 | 0.271 | 0.271 | 0.254 | 0.263 | 0.255 | 0.267 | 0.218 | 95 |

By 72 hours after treatment, the gamma- and delta-tocotrienol compositions show enhanced anti-proliferative effect, less than tocopherol succinate but much greater than geranylgeraniol, as seen in Table 5.

Table 5.

MTT assay results of BXPC3 cultures 120 hours (5 days) after treatment. The MTT assay was run 7 times, with the results from each run shown in the different columns. A blank was also tested. The final column shows the relative value set to the control of the 7 runs.

| run # | 1 | 2 | 3 | 4 | 5 | 6 | 7 | av | av-blank | rel amt |
|---|---|---|---|---|---|---|---|---|---|---|
| Blank | 0.052 | 0.054 | 0.056 | 0.055 | 0.055 | 0.059 | 0.055 | | | |
| Control | 0.626 | 0.613 | 0.62 | 0.618 | 0.67 | 0.626 | 0.642 | 0.631 | 0.576 | 100 |
| Vehicle | 0.641 | 0.644 | 0.647 | 0.653 | 0.669 | 0.659 | 0.648 | 0.652 | 0.597 | 104 |
| T3 alpha | 0.584 | 0.637 | 0.594 | 0.63 | 0.62 | 0.61 | 0.618 | 0.613 | 0.558 | 97 |
| T3 beta | 0.468 | 0.512 | 0.495 | 0.481 | 0.457 | 0.483 | 0.411 | 0.472 | 0.417 | 72 |
| T3 gamma | 0.418 | 0.446 | 0.446 | 0.457 | 0.428 | 0.412 | 0.42 | 0.432 | 0.377 | 66 |
| T3 delta | 0.485 | 0.49 | 0.522 | 0.539 | 0.551 | 0.523 | 0.527 | 0.520 | 0.465 | 81 |
| T alpha | 0.657 | 0.642 | 0.666 | 0.659 | 0.705 | 0.66 | 0.672 | 0.666 | 0.611 | 106 |
| T gamma | 0.628 | 0.66 | 0.653 | 0.649 | 0.682 | 0.615 | 0.661 | 0.650 | 0.595 | 103 |
| TS | 0.192 | 0.127 | 0.142 | 0.162 | 0.116 | 0.129 | 0.199 | 0.152 | 0.097 | 17 |
| GG | 0.621 | 0.655 | 0.672 | 0.663 | 0.657 | 0.724 | 0.66 | 0.665 | 0.610 | 106 |
| SA | 0.456 | 0.471 | 0.497 | 0.487 | 0.493 | 0.48 | 0.494 | 0.483 | 0.428 | 74 |

Figure 2:
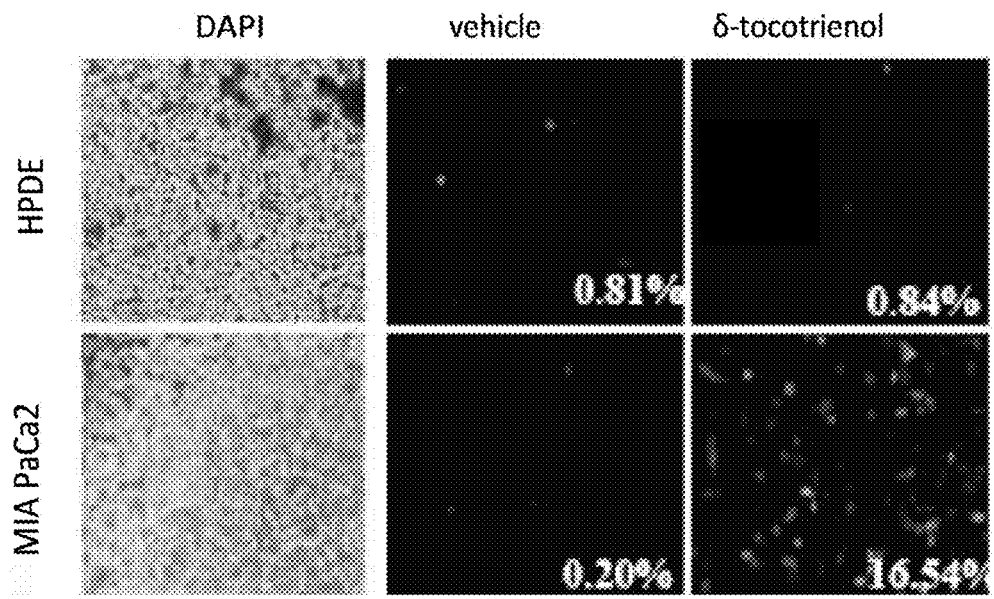
FIG. 2 is a series of images showing a significant increase in apoptotic cells in MIAPaCa2 treated with 50 μM δ-tocotrienol compared to vehicle or treated HPDE 6C7 cells. A pair t-test/one-way ANOVA FACS statistical software was used for the analysis. $p<0.05$.
Figure 3:
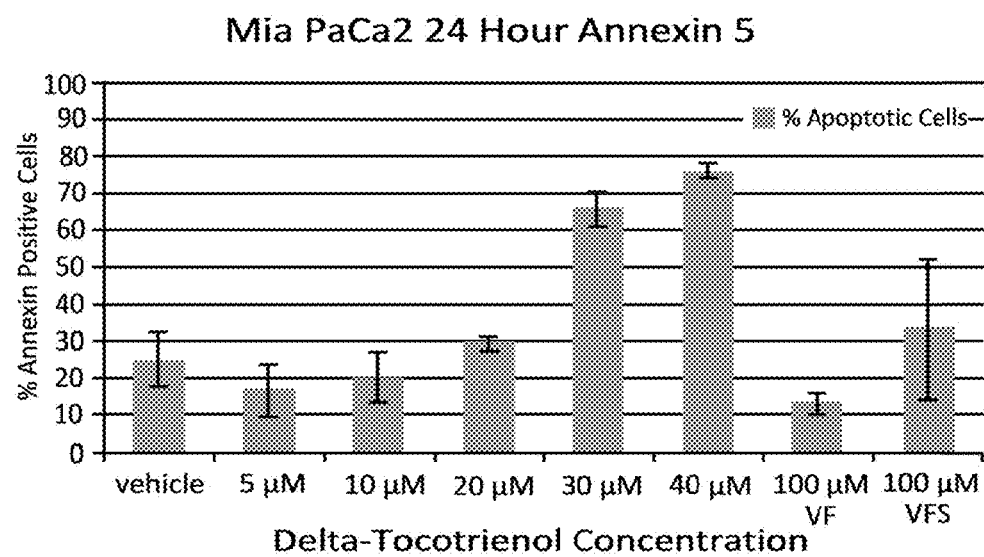
FIG. 3 is a graph wherein MIA PaCa-2 pancreatic cancer cells were treated with in varying concentrations of δ-tocotrienol or vehicle for 24 hours. Cells were collected and stained with Annexin V-FITC and analyzed by flow cytometry for apoptosis.
Figure 4:
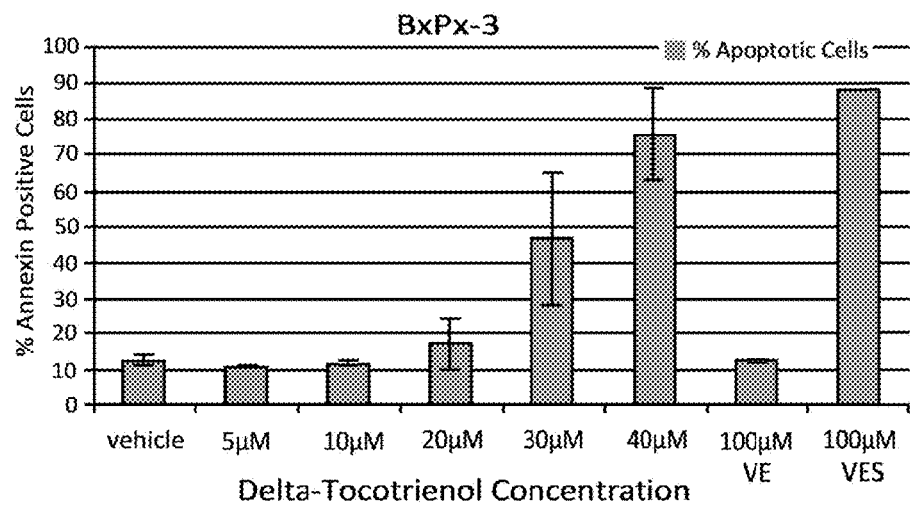
FIG. 4 is a graph wherein BXPC3 pancreatic cancer cells were treated with in varying concentrations of δ-tocotrienol or vehicle for 24 hours. Cells were collected and stained with Annexin V-FITC and analyzed by flow cytometry for apoptosis.
Figure 5:
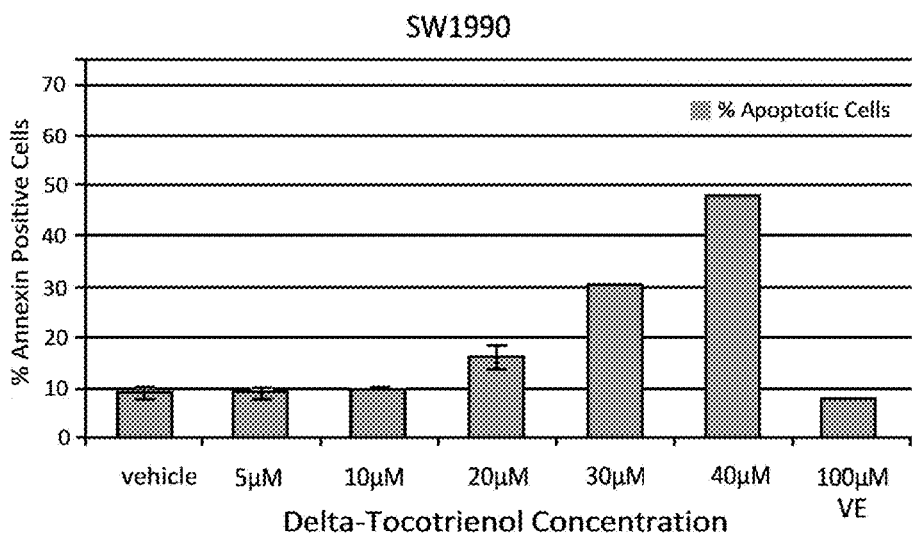
FIG. 5 is a graph wherein SW1990 pancreatic cancer cells were treated with in varying concentrations of δ-tocotrienol or vehicle for 24 hours. Cells were collected and stained with Annexin V-FITC and analyzed by flow cytometry for apoptosis.

MiaPaCa2 and HPDE 6C7 cells were cultured, as discussed above, and treated with δ-tocotrienol or vehicle. MIA-PaCa2 cells showed a significant increase in apoptotic cells after treatment with δ-tocotrienol as compared to vehicle or treated HPDE 6C7 cells, seen in FIG. 2. MiaPaCa-2, BxPc-3, and SW1990 pancreatic cancer cells were treated with in varying concentrations of δ-tocotrienol or vehicle for 24 hours. The cells were then harvested for annexin V-FITC staining and analyzed by flow cytometry. MiaPaCa-2 cells show a dose dependent induction of apoptosis upon treatment with δ-tocotrienol, as seen in FIG. 3. Similarly, BxPc-3, and SW1990 cells also displayed a dose dependent induction of apoptosis, as seen in FIGS. 4 and 5.

Figure 6:
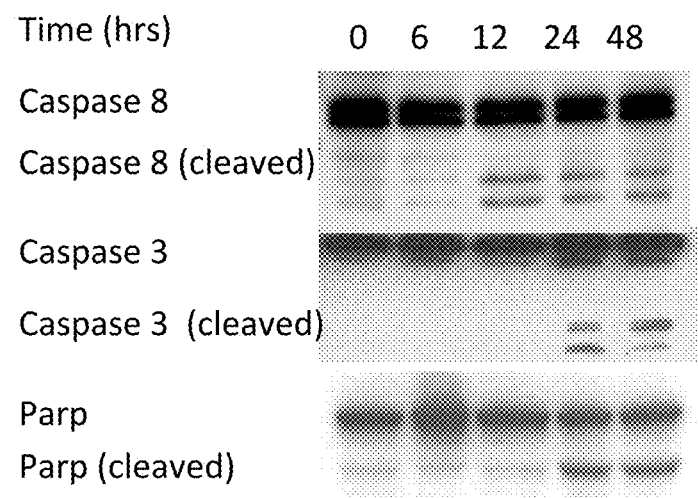
FIG. 6 shows activation of the caspase cascade as evidenced by cleavage of Caspase 8, Caspase 3, and PARP in a time dependent manner.
Figure 7:
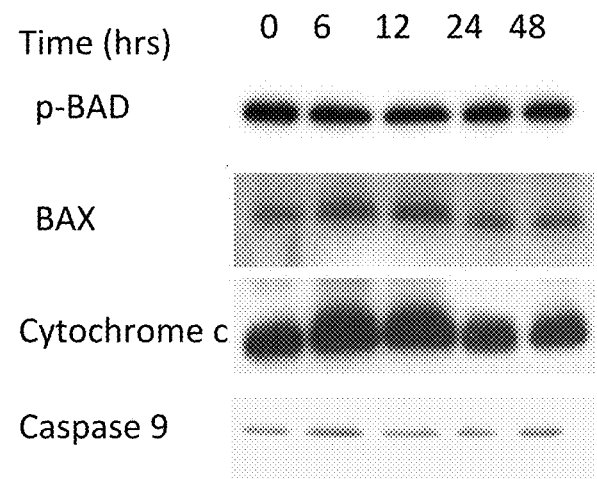
FIG. 7 shows MIA PaCa-2 cells treated with δ-tocotrienol had no significant effect on mitochondrial pro-apoptotic proteins as shown by a lack of cytochrome C release or cleavage of Caspase 9.
Figure 8:
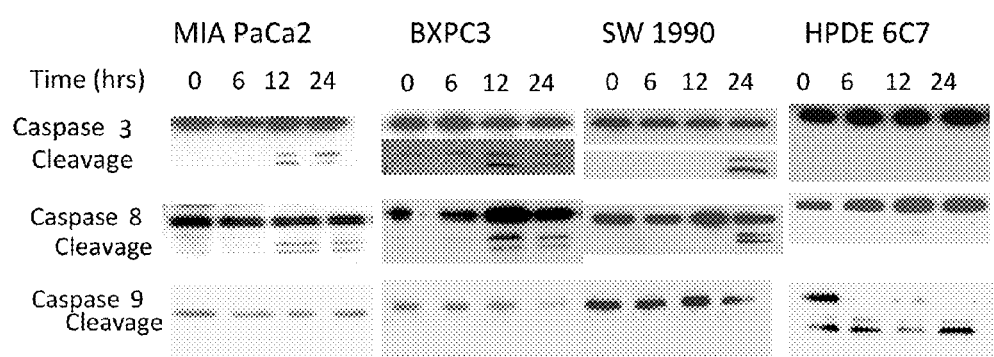
FIG. 8 shows selective caspase 8 and 3 cleavage in several pancreatic cancer cell lines but not in HPDE-6C7 cells, an immortalized pancreatic ductal epithelial cell line. Caspase 9 was not cleaved in the pancreatic cancer cells.
Figure 9:
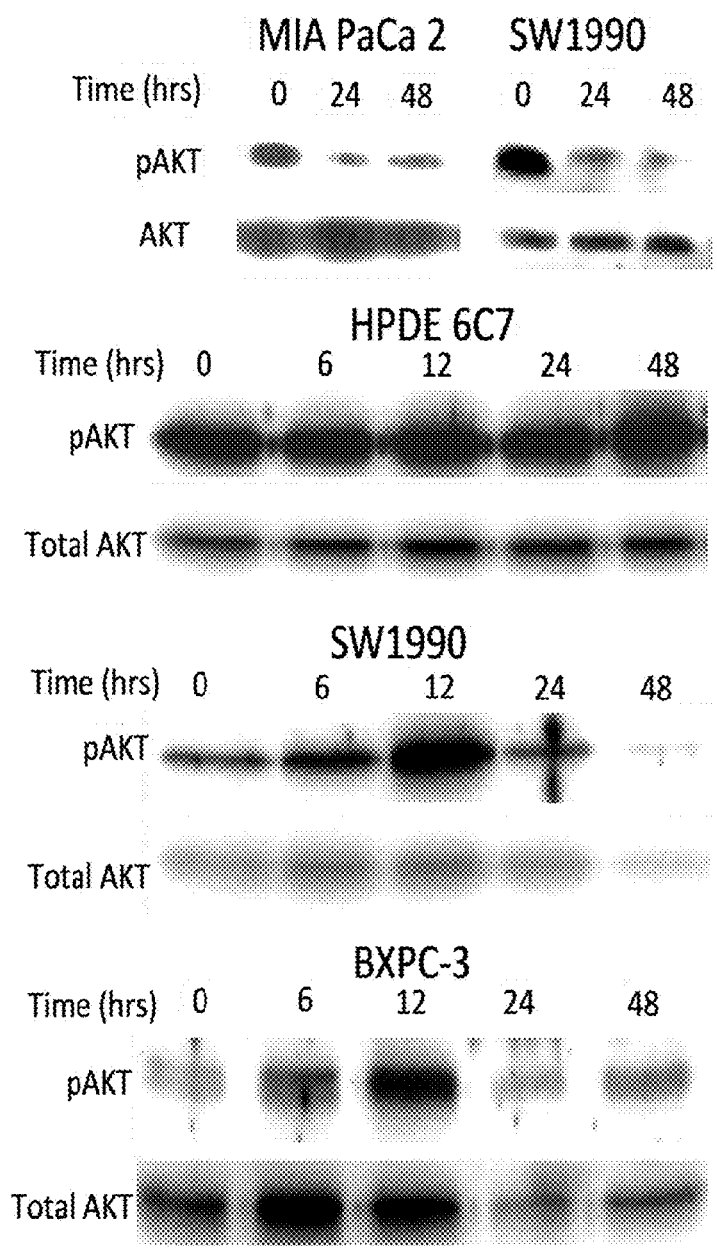
FIG. 9 shows a time-dependent decrease in phospho-AKT (but not total AKT) in the pancreatic cancer cell lines, but not in the HPDE cells.

The cultures were also tested for apoptotic activation through activation of the caspase cascade. An aliquot of the cells were collected and cells lysed. The lysate was then run on a Western blot and cleavage of caspase 8, caspase 3, and PARP detected. Caspase 8, caspase 3, and PARP showed cleavage in a time dependent manner, as seen in FIG. 6. Interestingly, MiaPaCa-2 cells treated with δ-tocotrienol had no significant effect on mitochondrial pro-apoptotic proteins as shown by a lack of cytochrome C release or cleavage of caspase 9, seen in FIG. 7. caspase 9 was not cleaved in the pancreatic cancer cells. FIG. 8 shows selective caspase 8 and 3 cleavage in several pancreatic cancer cell lines but not in HPDE-6C7 cells, an immortalized pancreatic ductal epithelial cell line. FIG. 9 shows a time-dependent decrease in phospho-AKT (but not total AKT) in the pancreatic cancer cell lines, but not in the HPDE cells.

Example 3

MiaPaCa-2 cells were cultured in complete DMEM media containing 10% fetal bovine serum (FBS) and 1% penicillin-streptomycin, and 1% L-glutamine. BxPc-3 pancreatic cancer cells were cultured in complete RPMI media containing 10% fetal bovine serum (FBS), and 1% penicillin-streptomycin, 1% HEPES buffer, 1% sodium pyruvate and 1% L-glutamine HPDE6-C7 cells were cultured in serum-free keratinocyte SFM media. All cells were maintained at 37° C. in a humidified incubator with 5% $CO_2$. The cells were treated with a single 50 μM dose of vehicle (vehicle only, may be a solvent), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). A control (no treatment) culture was grown alongside the treatments for comparison. Cell viability was measured using MTT assay at preselect times of 48 or 120 hours after treatment. At 48 hours there is minimal effect from the different compositions, as seen by Table 6.

Table 6.

MTS assay results of MiaPaCa2 cultures 24 hours after treatment. The MTS assay was run 9 times, with the results from each run shown in the different columns. The final column shows the relative value set to the control of the 9 runs.

| run # | 1 | 2 | 3 | 4 | 5 | 6 | 7 | 8 | 9 | rel amt |
|---|---|---|---|---|---|---|---|---|---|---|
| Control | 0.225 | 0.226 | 0.223 | 0.216 | 0.239 | 0.204 | 0.226 | 0.219 | 0.222 | 100 |
| Vehicle | 0.266 | 0.238 | 0.225 | 0.192 | 0.183 | 0.2 | 0.189 | 0.198 | 0.211 | 95 |
| T3 alpha | 0.274 | 0.296 | 0.293 | 0.216 | 0.245 | 0.258 | 0.243 | 0.239 | 0.258 | 116 |
| T3 beta | 0.17 | 0.179 | 0.184 | 0.152 | 0.172 | 0.182 | 0.179 | 0.19 | 0.176 | 79 |
| T3 gamma | 0.133 | 0.135 | 0.141 | 0.127 | 0.142 | 0.166 | 0.171 | 0.162 | 0.147 | 66 |
| T3 delta | 0.174 | 0.159 | 0.171 | 0.139 | 0.185 | 0.187 | 0.18 | 0.167 | 0.170 | 77 |
| T alpha | 0.249 | 0.25 | 0.253 | 0.207 | 0.253 | 0.238 | 0.27 | 0.254 | 0.247 | 111 |
| T gamma | 0.273 | 0.261 | 0.268 | 0.219 | 0.264 | 0.31 | 0.295 | 0.263 | 0.269 | 121 |
| TS | 0.24 | 0.211 | 0.226 | 0.172 | 0.221 | 0.201 | 0.214 | 0.228 | 0.214 | 96 |
| GG | 0.186 | 0.166 | 0.175 | 0.18 | 0.196 | 0.199 | 0.184 | 0.178 | 0.183 | 82 |
| SA | 0.24 | 0.248 | 0.25 | 0.245 | 0.236 | 0.219 | 0.214 | 0.204 | 0.232 | 105 |

The tocotrienols, particularly beta and delta, show reduced cell viability by 48 hours, as seen in Table 7. Notably, the beta-, gamma-, and delta-tocotrienol show comparable or improved anti-proliferative effects as compared to the chemotherapeutics geranylgeraniol and tocopherol succinate.

Table 7.

MTS assay results of MiaPaCa2 cultures 48 hours after treatment. The MTS assay was run 9 times, with the results from each run shown in the different columns. The final column shows the relative value set to the control of the 9 runs.

| run # | 1 | 2 | 3 | 4 | 5 | 6 | 7 | 8 | 9 | rel amt |
|---|---|---|---|---|---|---|---|---|---|---|
| Control | 0.364 | 0.354 | 0.321 | 0.362 | 0.416 | 0.296 | 0.382 | 0.397 | 0.362 | 100 |
| Vehicle | 0.374 | 0.357 | 0.356 | 0.331 | 0.382 | 0.389 | 0.396 | 0.335 | 0.365 | 101 |
| T3 alpha | 0.336 | 0.325 | 0.343 | 0.327 | 0.39 | 0.376 | 0.322 | 0.286 | 0.338 | 93 |
| T3 beta | 0.193 | 0.137 | 0.227 | 0.223 | 0.231 | 0.272 | 0.225 | 0.27 | 0.222 | 61 |
| T3 gamma | 0.095 | 0.116 | 0.111 | 0.128 | 0.159 | 0.147 | 0.167 | 0.152 | 0.134 | 37 |
| T3 delta | 0.229 | 0.22 | 0.218 | 0.232 | 0.294 | 0.272 | 0.221 | 0.243 | 0.241 | 67 |
| T alpha | 0.308 | 0.313 | 0.342 | 0.269 | 0.352 | 0.277 | 0.305 | 0.339 | 0.313 | 86 |
| T gamma | 0.329 | 0.265 | 0.304 | 0.25 | 0.289 | 0.341 | 0.301 | 0.279 | 0.295 | 81 |
| TS | 0.257 | 0.254 | 0.262 | 0.237 | 0.258 | 0.275 | 0.32 | 0.337 | 0.275 | 76 |
| GG | 0.154 | 0.194 | 0.181 | 0.198 | 0.236 | 0.198 | 0.193 | 0.192 | 0.193 | 53 |
| SA | 0.334 | 0.335 | 0.333 | 0.304 | 0.32 | 0.294 | 0.352 | 0.348 | 0.328 | 90 |

Figure 10:
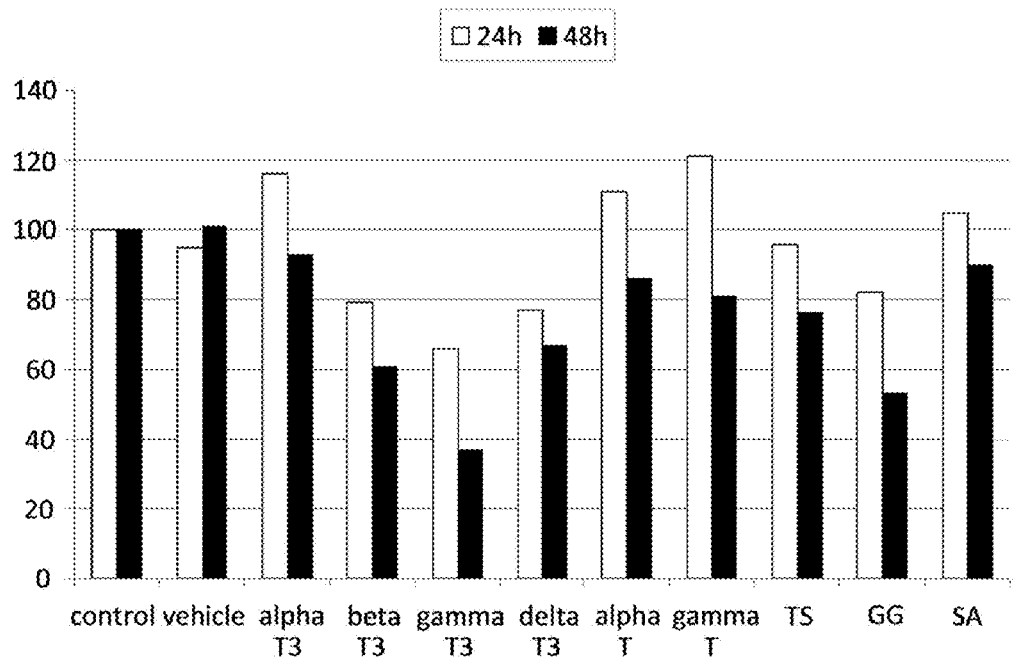
FIG. 10 is a graph of the MTS analysis of MiaPaCa2 pancreatic cancer cells, 24 and 48 hours, shown in Tables IV-V.

The tocotrienols, particularly beta and delta, show reduced cell viability by 48 hours, as seen in Table 8. Notably, the gamma- and delta-tocotrienol show comparable or improved anti-proliferative effects as compared to the chemotherapeutic geranylgeraniol. These results are further illustrated in FIG. 10, which represents the results for the 24 hour and 48 hour trials Table 8.

MTS assay results of MiaPaCa2 cultures 72 hours after treatment. The MTS assay was run 9 times, with the results from each run shown in the different columns. The final column shows the relative value set to the control of the 9 runs.

| run # | 1 | 2 | 3 | 4 | 5 | 6 | 7 | 8 | 9 | rel amt |
|---|---|---|---|---|---|---|---|---|---|---|
| Control | 0.464 | 0.511 | 0.447 | 0.421 | 0.428 | 0.42 | 0.43 | 0.433 | 0.444 | 100 |
| Vehicle | 0.409 | 0.358 | 0.353 | 0.321 | 0.345 | 0.304 | 0.322 | 0.336 | 0.344 | 77 |
| T3 alpha | 0.279 | 0.282 | 0.294 | 0.238 | 0.302 | 0.279 | 0.254 | 0.254 | 0.273 | 61 |
| T3 beta | 0.349 | 0.316 | 0.328 | 0.298 | 0.323 | 0.287 | 0.281 | 0.275 | 0.307 | 69 |
| T3 gamma | 0.776 | 0.744 | 0.876 | 0.734 | 0.812 | 0.817 | 0.773 | 0.759 | 0.786 | 177 |
| T3 delta | 0.667 | 0.615 | 0.605 | 0.587 | 0.582 | 0.491 | 0.524 | 0.604 | 0.584 | 132 |
| T alpha | 0.523 | 0.478 | 0.464 | 0.453 | 0.443 | 0.456 | 0.383 | 0.451 | 0.456 | 103 |
| T gamma | 0.5 | 0.497 | 0.46 | 0.505 | 0.515 | 0.469 | 0.429 | 0.451 | 0.478 | 108 |
| TS | 0.998 | 0.962 | 1.016 | 0.887 | 0.936 | 0.897 | 0.85 | 0.801 | 0.918 | 207 |
| GG | 0.784 | 0.713 | 0.757 | 0.734 | 0.682 | 0.665 | 0.65 | 0.627 | 0.702 | 158 |
| SA | 0.596 | 0.547 | 0.566 | 0.515 | 0.544 | 0.44 | 0.397 | 0.427 | 0.504 | 114 |

MiaPaCa-2, BxPc-3, and HPDE6-C7 cells were cultured as described above, and treated with a single 50 μM dose of vehicle (ethanol extracted olive oil), T3 alpha (alpha tocotrienol), T3 beta (beta tocotrienol), T3 gamma (gamma tocotrienol), T3 delta (delta tocotrienol), T alpha (alpha tocopherol), T beta (beta tocopherol), TS (tocopherol succinate), GG (geranylgeraniol), SA (succinic acid). A control culture (vehicle only with no treatment) was grown alongside the treatments for comparison. Cell viability was measured using MTT assay at preselect times of 48 or 120 hours after treatment. At 48 hours there is minimal effect from the different compositions, as seen by Tables 9 and 10.

Table 9.

MTT assay results of MiaPaCa2 cultures 48 hours after treatment. The MTT assay was run 7 times, with the results from each run shown in the different columns. A blank was also tested. The final column shows the relative value set to the control of the 7 runs.

| run # | 1 | 2 | 3 | 4 | 5 | 6 | 7 | av | av-blank | rel amt |
|---|---|---|---|---|---|---|---|---|---|---|
| Blank | 0.047 | 0.048 | 0.048 | 0.045 | 0.049 | 0.041 | 0.046 | | | |
| Control | 0.384 | 0.372 | 0.341 | 0.333 | 0.382 | 0.345 | 0.332 | 0.356 | 0.310 | 100 |
| Vehicle | 0.342 | 0.315 | 0.309 | 0.342 | 0.347 | 0.321 | 0.306 | 0.326 | 0.280 | 90 |
| T3 alpha | 0.349 | 0.341 | 0.356 | 0.329 | 0.349 | 0.316 | 0.323 | 0.338 | 0.292 | 94 |
| T3 beta | 0.272 | 0.235 | 0.233 | 0.226 | 0.252 | 0.219 | 0.239 | 0.239 | 0.193 | 62 |
| T3 gamma | 0.185 | 0.181 | 0.156 | 0.183 | 0.21 | 0.141 | 0.137 | 0.170 | 0.124 | 40 |

-continued

| run # | 1 | 2 | 3 | 4 | 5 | 6 | 7 | av | av-blank | rel amt |
|---|---|---|---|---|---|---|---|---|---|---|
| T3 delta | 0.276 | 0.284 | 0.262 | 0.239 | 0.275 | 0.239 | 0.269 | 0.263 | 0.217 | 70 |
| T alpha | 0.365 | 0.352 | 0.339 | 0.338 | 0.35 | 0.297 | 0.35 | 0.342 | 0.296 | 95 |
| T gamma | 0.35 | 0.323 | 0.312 | 0.36 | 0.348 | 0.328 | 0.348 | 0.338 | 0.292 | 94 |
| TS | 0.215 | 0.184 | 0.2 | 0.187 | 0.194 | 0.19 | 0.185 | 0.194 | 0.148 | 48 |
| GG | 0.329 | 0.339 | 0.321 | 0.328 | 0.342 | 0.317 | 0.341 | 0.331 | 0.285 | 92 |
| SA | 0.276 | 0.269 | 0.268 | 0.276 | 0.3 | 0.262 | 0.266 | 0.274 | 0.228 | 74 |

Table 10.

MTT assay results of MiaPaCa2 cultures 120 hours (5 days) after treatment. The MTT assay was run 7 times, with the results from each run shown in the different columns. A blank was also tested. The final column shows the relative value set to the control of the 7 runs.

| run # | 1 | 2 | 3 | 4 | 5 | 6 | 7 | av | av-blank | rel amt |
|---|---|---|---|---|---|---|---|---|---|---|
| Blank | 0.051 | 0.052 | 0.052 | 0.052 | 0.052 | 0.053 | 0.052 | | | |
| Control | 1.803 | 1.86 | 1.75 | 1.832 | 2.241 | 1.751 | 1.79 | 1.861 | 1.809 | 100 |
| Vehicle | 1.733 | 1.661 | 1.594 | 1.754 | 2.161 | 1.703 | 1.68 | 1.755 | 1.703 | 94 |
| T3 alpha | 1.497 | 1.573 | 1.569 | 1.55 | 1.811 | 1.589 | 1.47 | 1.580 | 1.528 | 84 |
| T3 beta | 0.97 | 0.781 | 0.977 | 1.154 | 1.408 | 0.944 | 0.891 | 1.018 | 0.966 | 53 |
| T3 gamma | 0.088 | 0.084 | 0.098 | 0.089 | 0.12 | 0.084 | 0.092 | 0.094 | 0.042 | 2 |
| T3 delta | 1.344 | 1.314 | 1.27 | 1.337 | 1.579 | 1.308 | 1.341 | 1.356 | 1.304 | 72 |
| T alpha | 1.56 | 1.647 | 1.59 | 1.619 | 2.059 | 1.526 | 1.588 | 1.656 | 1.604 | 89 |
| T gamma | 1.52 | 1.516 | 1.547 | 1.625 | 1.917 | 1.568 | 1.635 | 1.618 | 1.566 | 87 |
| TS | 0.732 | 0.776 | 0.786 | 0.714 | 0.939 | 0.859 | 0.968 | 0.825 | 0.773 | 43 |
| GG | 1.738 | 1.608 | 1.577 | 1.744 | 2.134 | 1.606 | 1.711 | 1.731 | 1.679 | 93 |
| SA | 1.36 | 1.346 | 1.488 | 1.609 | 1.84 | 1.412 | 1.408 | 1.495 | 1.443 | 80 |

Figure 11A:
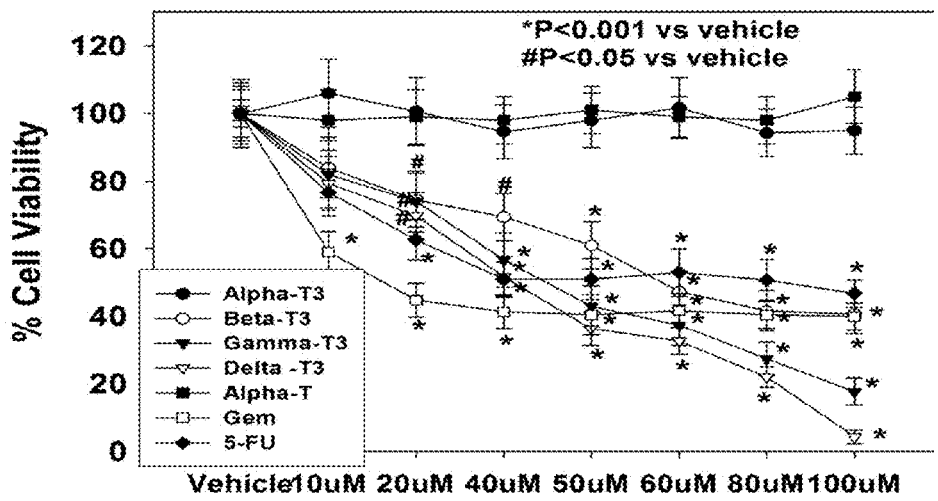
FIGS. 11A and B are graphs showing the effect of tocotrienols on pancreatic cancer proliferation (MTT). The presence of 40 to 100 μM of δ-tocotrienol significantly decreased the proliferation of both MiaPaCa2 (A) and AsPc1 (B) pancreatic cancer cells at 72 hours, as compared with vehicle treated cells and cells treated with β-, or γ-tocotrienol as well as gemcitabine and 5-fluorouracil treated cells. In contrast, no effect was observed with α-tocopherol or α-tocotrienol treated cells. Points, means; bars, SE (n=3).

However, assaying the cells at 72 hours show that beta-, gamma-, and delta-tocotrienol had a concentration-dependent effect on cell viability, with δ-tocotrienol exhibiting the most effective inhibition of pancreatic cancer proliferation as shown in FIGS. 11A and B.

Example 4

Figure 11B:
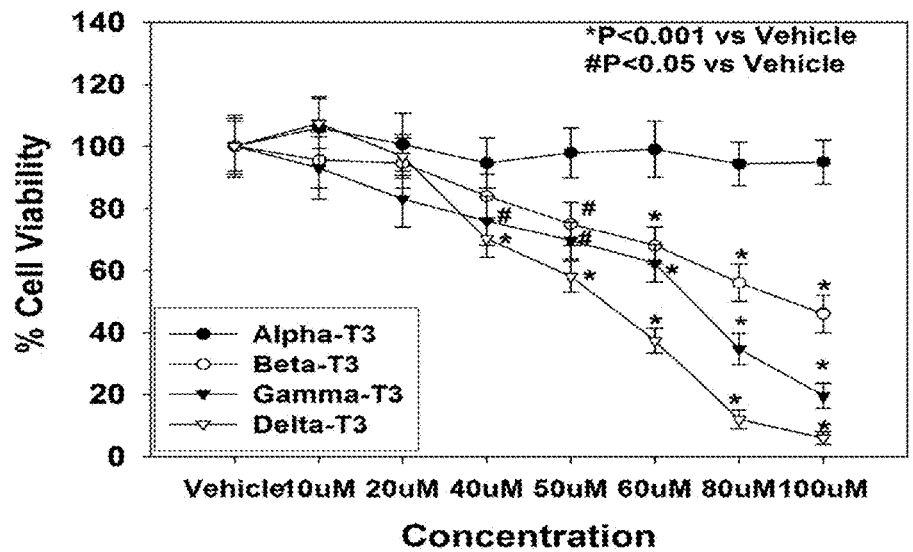

To further identify the role of AKT in the apoptotic pathways noted in Example 2, functional overexpression of CA-AKT was analyzed in Mia-PaCa2 pancreatic cancer cells. MIA PaCa-2 cells were treated with pZWL vector and myrAKT, a retroviral vector encoding myristoylated AKT, with or without serum, vehicle, or δ-tocotrienol (40 or 50 µM) for 24 hours, with and without a 10-hour caspase 8 inhibitor pretreatment. Cells were also treated with TRAIL as a positive control. Cells were then harvested, fixed, permeablized and stained with trypan blue. Western blot of cell lysates from FIG. 12 demonstrate the decrease of pAKT with 50 uM treatment of tocotrienol in MiaPaca 2 parenteral cells transfected with empty vector compared to cells overexpressing constitutively active AKT, as seen in FIG. 11.

Figure 12:
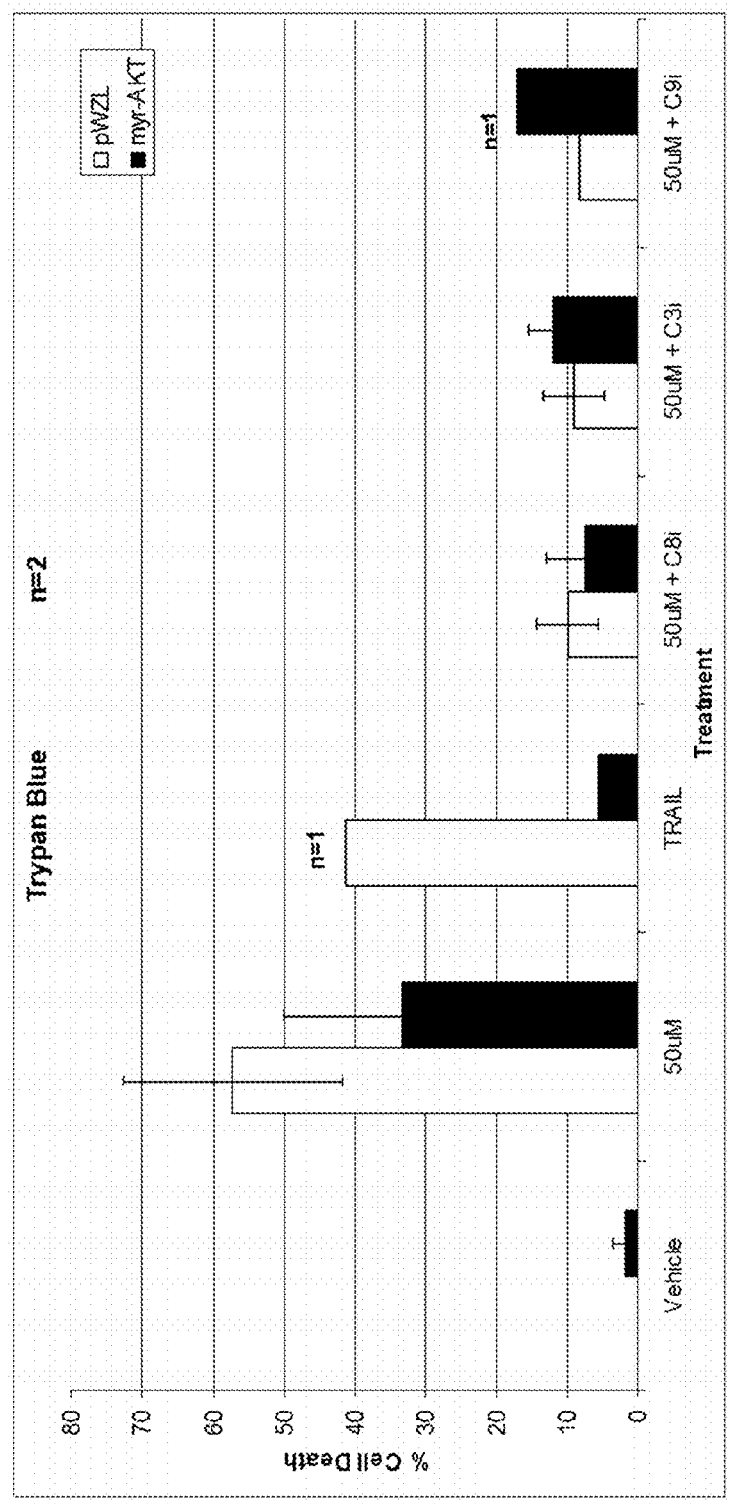
FIG. 12 is a graph wherein MIA PaCa-2 cells (pZWL vector and myrAKT) were treated without serum vehicle or δ-tocotrienol (50 μM) for 24 hours, with and without a 10-hour caspase 8/3 inhibitor pretreatment. Cells were also treated with TRAIL as a positive control. Cells were then harvested, fixed, permeablized and stained with trypan blue. The graph shows a significant increase in apoptotic cells in vector compared to vehicle, myr-AKT, or caspase 8/3 inhibitor treated cells.
Figure 13:
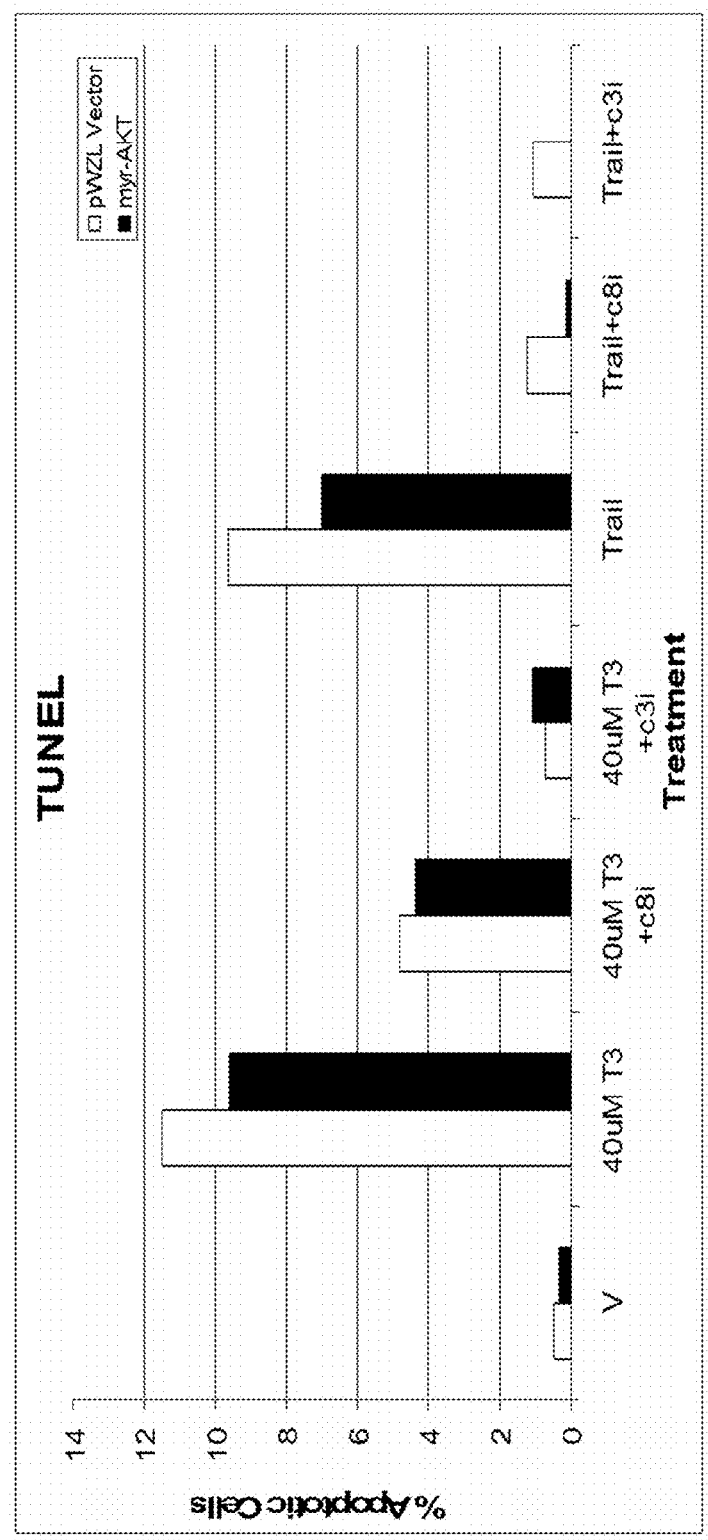
FIG. 13 is a graph wherein MIA PaCa-2 cells (pZWL vector and myrAKT) were treated without serum vehicle or δ-tocotrienol (40 μM) for 24 hours, with and without a 10-hour caspase 8/3 inhibitor pretreatment. Cells were then harvested, fixed, permeablized and stained for Tunel. The graph shows a significant increase in apoptotic cells in vector compared to vehicle, myr-AKT, or caspase 8/3 inhibitor treated cells.
Figure 14:
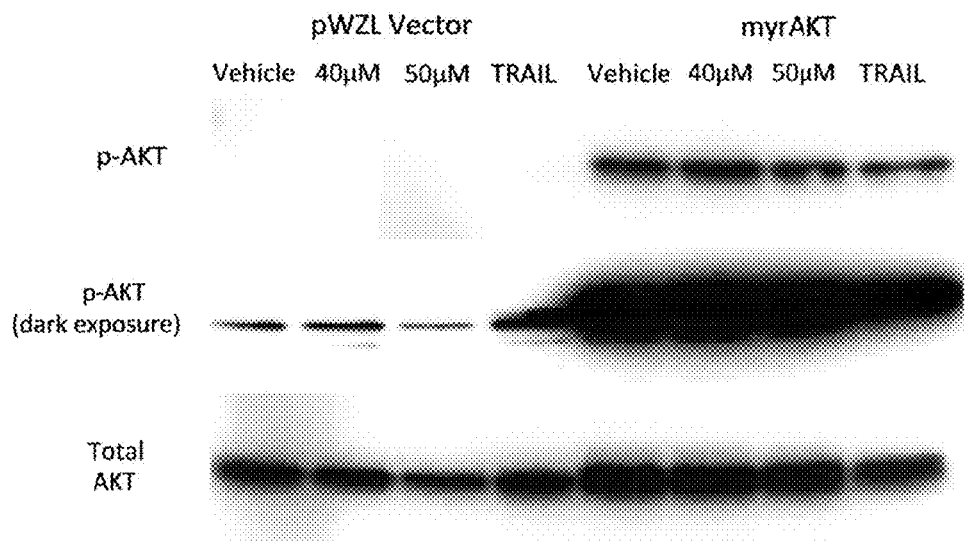
FIG. 14 is a series of blots demonstrating the rescue of δ-Tocotrienol suppression PI3K-AKT signaling after infection of Mia-PaCa2 pancreatic cancer cells with pWZL retroviral vector encoding myristoylated AKT.
Figure 15:
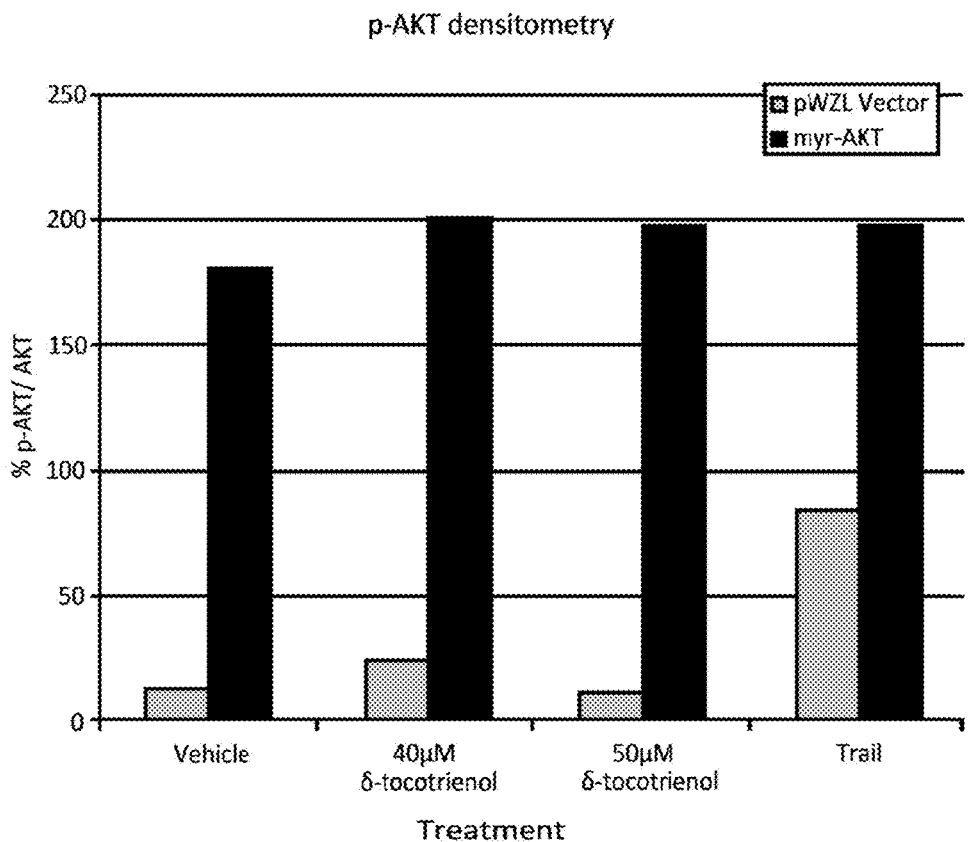
FIG. 15 is a graph of pAKT densitometry, demonstrating the rescue of δ-Tocotrienol suppression PI3K-AKT signaling after infection of Mia-PaCa2 pancreatic cancer cells with pWZL retroviral vector encoding myristoylated AKT.
Figure 16:
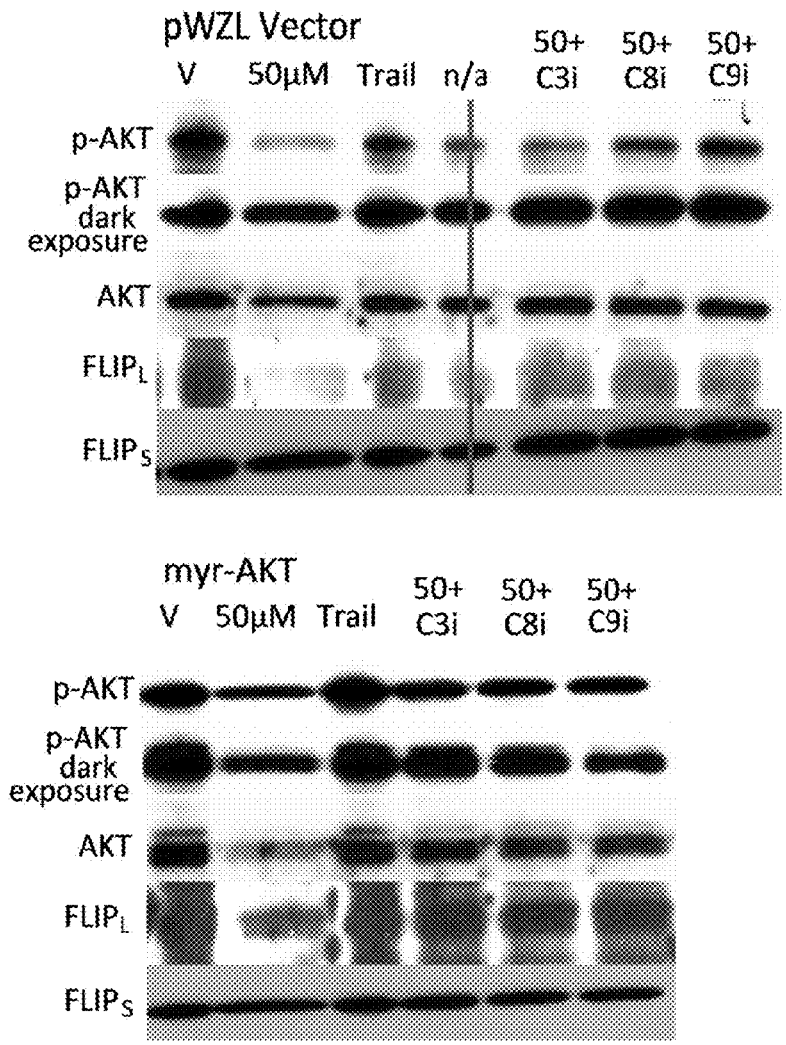
FIG. 16 is a series of blots showing that delta-tocotrienol modulates AKT signaling. Mia-PaCa2 pancreatic cancer cells with pWZL retroviral vector encoding myristoylated AKT.
Figure 17:
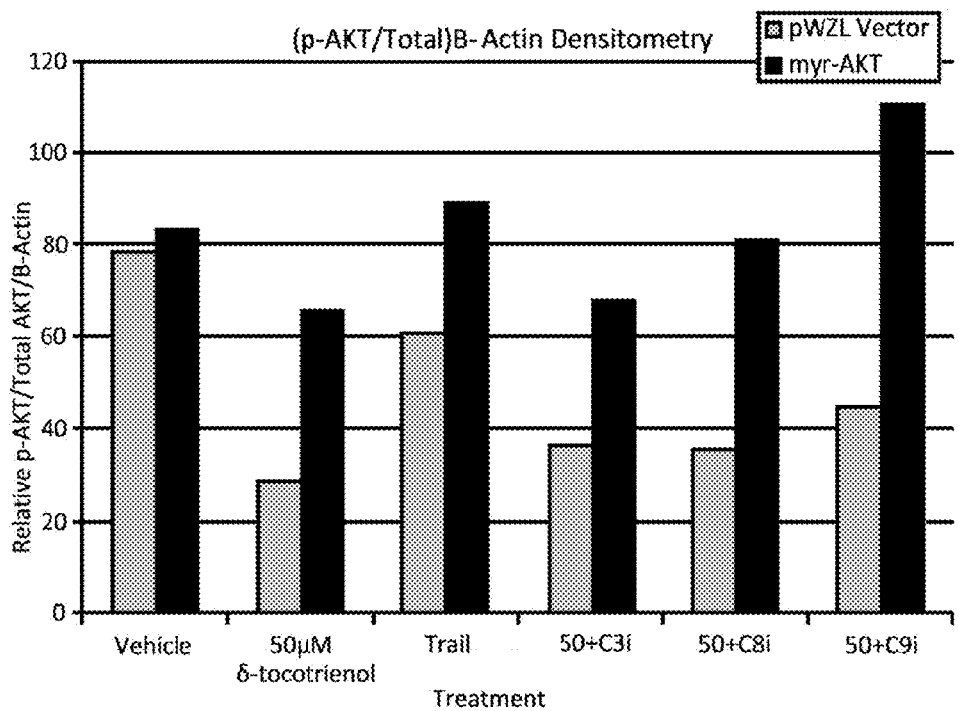
FIG. 17 is a graph showing (p-AKT/Total)/B-actin densitometry.
Figure 18:
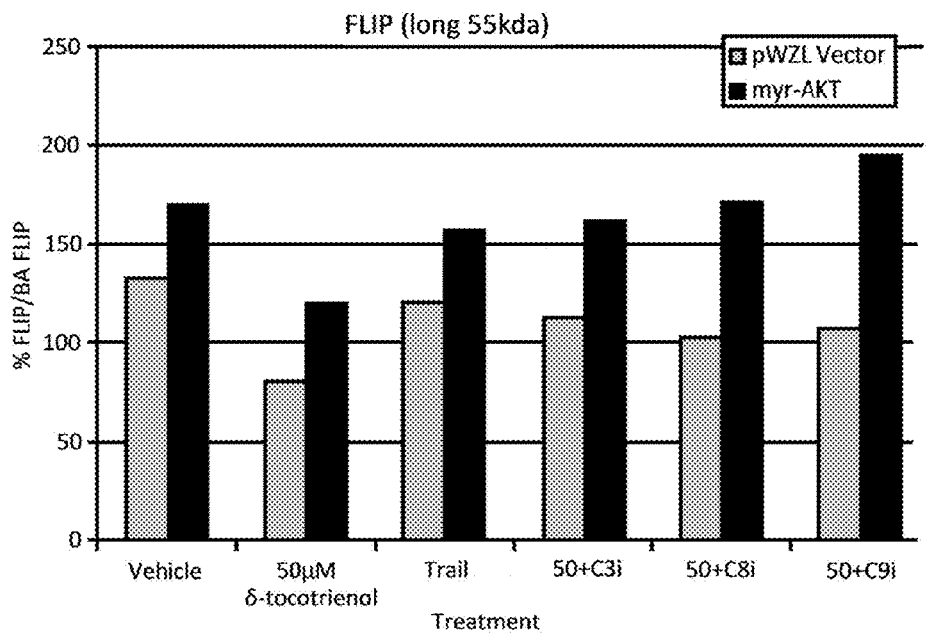
FIG. 18 is a graph showing % FLIP(long 55 kda)/B-actin densitometry.
Figure 19:
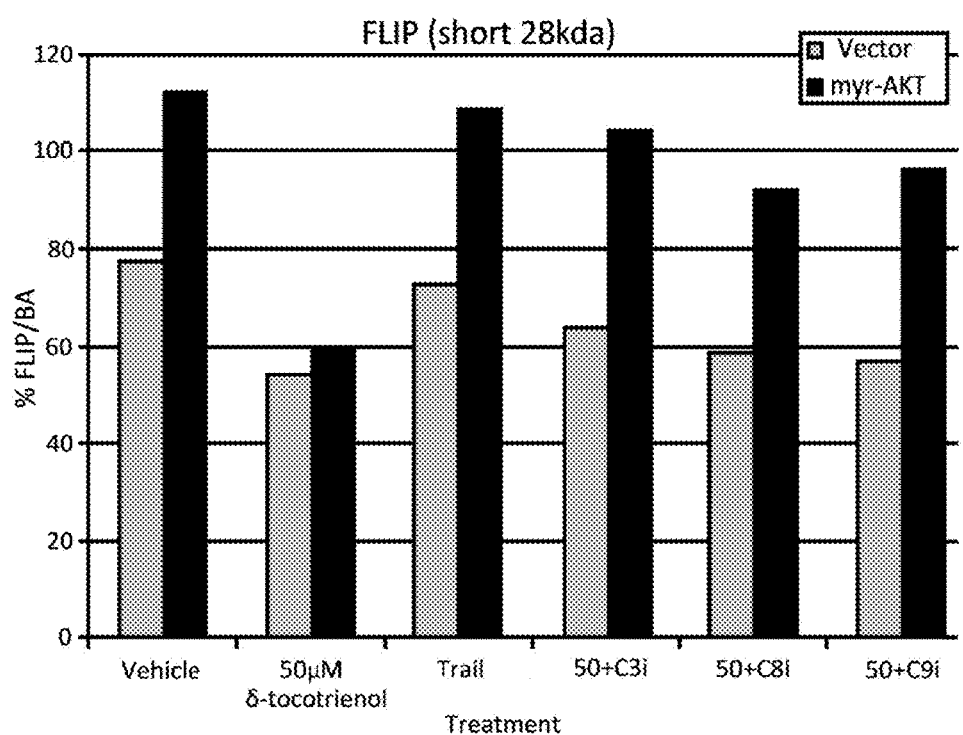
FIG. 19 is a graph showing % FLIP(short 28 kda)/B-actin densitometry.

Overexpression of CA-AKT demonstrates the role of AKT signaling and caspase 8 in δ-tocotrienol-induced cell death, as seen in FIG. 12. The myristoylated AKT rescued δ-tocotrienol suppression PI3K-AKT signaling. The MiaPaCa-2 parental cell lines were stably transfected using constitutively active myristoylated AKT in a pWZL vector construct to generate MiaPaCa-2$_{AKT}$ cells. FIGS. 14 and 15 demonstrate the rescue of δ-tocotrienols ability to downregulate p-AKT. Further, AKT and caspase 8/3 pathways are involved in the mechanism by which tocotrienol induces cell death, as seen in FIGS. 16 through 19. Treatment with tocotrienol induced more cell death in the vector cells than the myr-AKT cells when compared to vehicle. TRAIL induced cell death was comparable to vehicle. Lastly, pretreatment with caspase 3, 8 and 9 inhibitors rescued tocotrienol induced cell death.

Example 5

Figure 20:
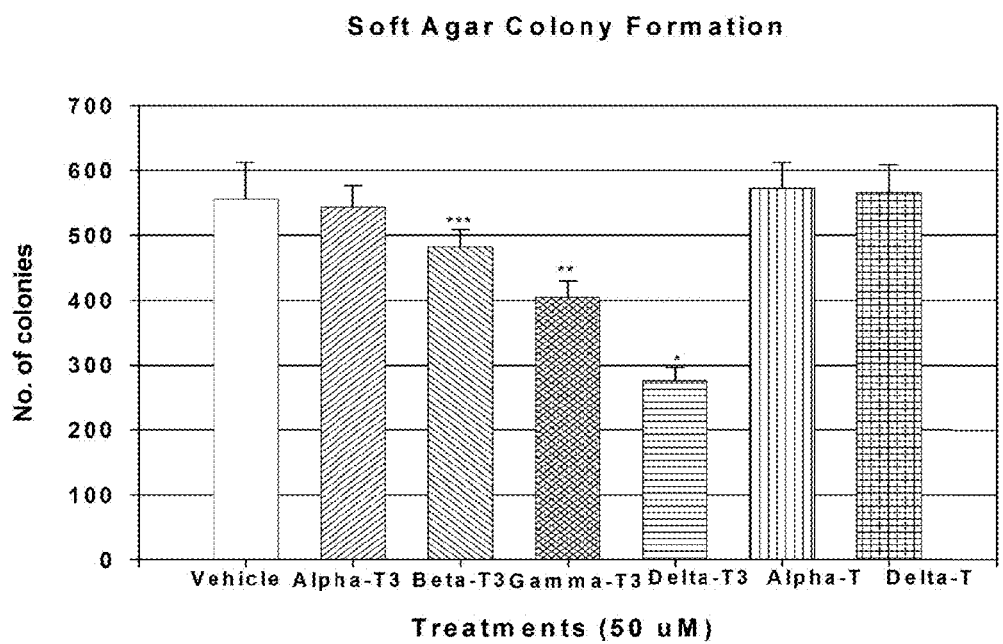
FIG. 20 is a graph showing the effect of tocotrienols on pancreatic cancer malignant transformation (Soft Agar). The presence of 50 μM δ-tocotrienol significantly inhibited the malignant transformation of MiaPaCa2 pancreatic cancer cells as compared with vehicle treated cells and cells treated with β-, or γ-tocotrienol. In contrast, no effect was observed with α-tocopherol, δ-tocopherol, or α-tocotrienol treated cells. Bars, SE (n=3). *p<0.001 vs. vehicle. p<0.02 vs. vehicle. *p<0.05 vs. vehicle. T=tocopherol, T3=tocotrienol.

MiaPaCa2 cells ($3 \times 10^3$) were cultured as described in the Examples above, in 96-well plates and treated with 50 µM of different tocopherol or tocotrienol. The colony formation was counted, showing that δ-tocotrienol was the most effective tocotrienol in inhibiting pancreatic cancer malignant transformation, as seen in FIG. 20.

Figure 21:
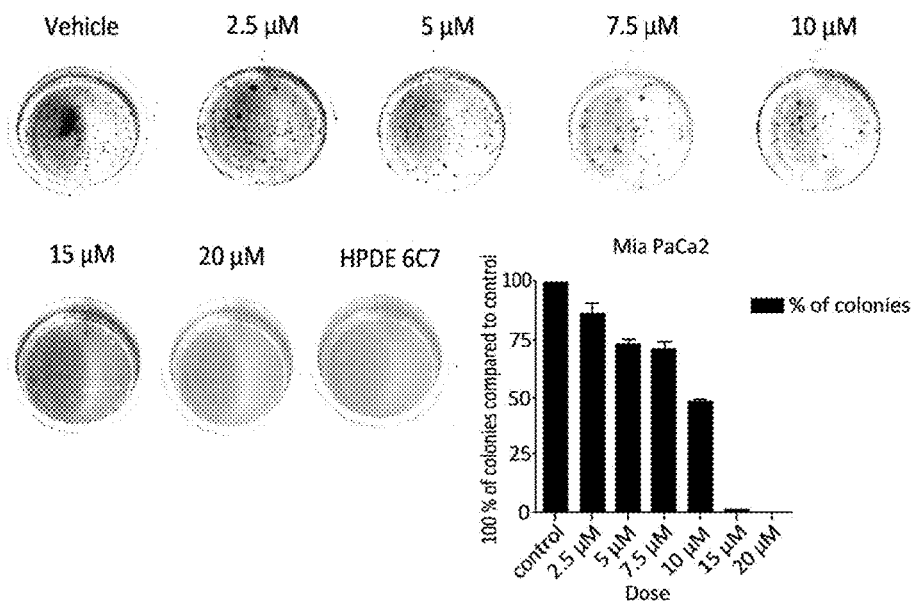
FIG. 21 is an image of MIA PaCa2 cells in soft agar; significant inhibition of anchorage independent growth of cells occurred when treated with weekly δ-tocotrienol compared to vehicle.
Figure 22:
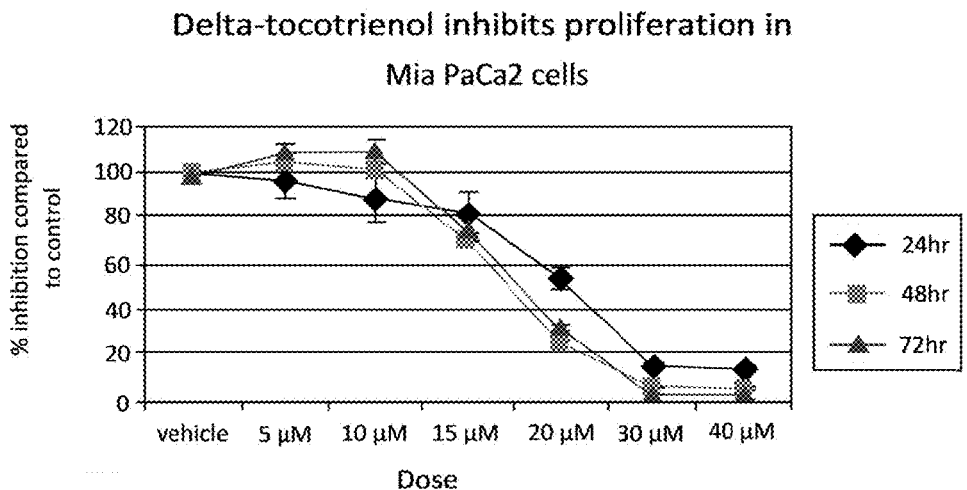
FIG. 22 is a graph wherein MIA PaCa2 pancreatic cancer cells (3×10³) were plated in 96 well plates and treated the following day with δ-tocotrienol. Proliferation was assessed by MTT at 24 hour intervals. Results show a dose dependent inhibition of proliferation. The $IC_{50}$ for all three pancreatic cancer cell lines was 20-25 μM at 24 hours. HPDE 6C7 cells were also treated with increasing concentrations of δ-tocotrienol for 24 hours.
Figure 23:
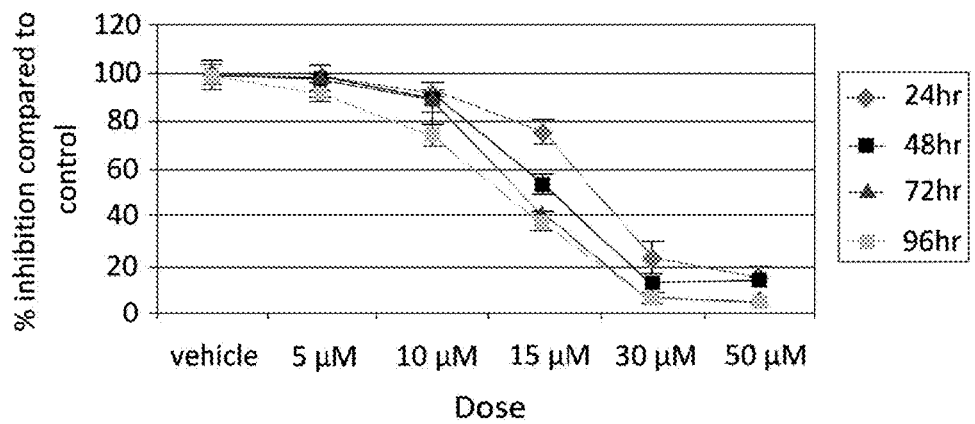
FIG. 23 is a graph wherein SW1990 pancreatic cancer cells (3×10³) were plated in 96 well plates and treated the following day with δ-tocotrienol. Proliferation was assessed by MTT at 24 hour intervals. Results show a dose dependent inhibition of proliferation. The $IC_{50}$ for all three pancreatic cancer cell lines was 20-25 μM at 24 hours. HPDE 6C7 cells were also treated with increasing concentrations of δ-tocotrienol for 24 hours.
Figure 24:
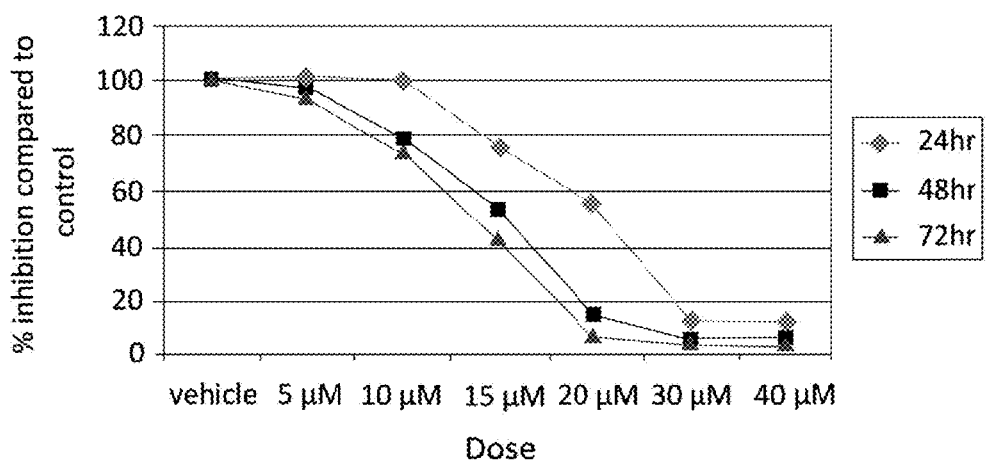
FIG. 24 is a graph wherein BXPC3 pancreatic cancer cells (3×10³) were plated in 96 well plates and treated the following day with δ-tocotrienol. Proliferation was assessed by MTT at 24 hour intervals. Results show a dose dependent inhibition of proliferation. The $IC_{50}$ for all three pancreatic cancer cell lines was 20-25 μM at 24 hours. HPDE 6C7 cells were also treated with increasing concentrations of δ-tocotrienol for 24 hours.
Figure 25:
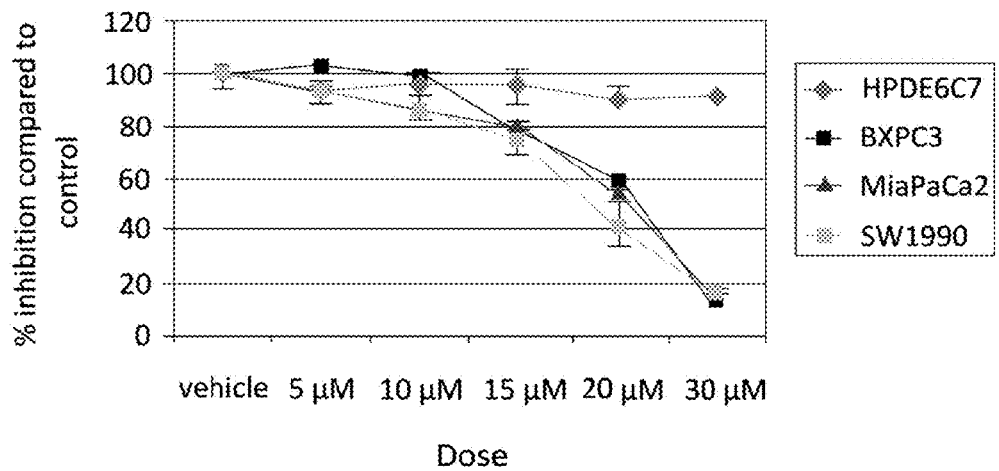
FIG. 25 is a graph showing selective inhibition of proliferation of pancreatic cancer cell lines by δ-tocotrienol at 24 hours. HPDE 6C7 cells were relatively resistant to the antiproliferative effects of tocotrienol, even at the highest concentrations.

MIA PaCa2, SW1990, BXPC3, and HPDE 6C7 cells ($3 \times 10^3$) were cultured as described in the Examples above, in 96-well plates and treated the following day with increasing concentrations of δ-tocotrienol. FIG. 21 shows significant inhibition of anchorage independent growth of MIA PaCa2 cells in soft agar when treated with weekly δ-tocotrienol compared to vehicle. HPDE 6C7 cells grown in recommended media alone did not undergo transformation in soft agar, as would be expected in this preneoplastic cell line, and served as a negative control. Proliferation was assessed by MTT at 24 hour intervals, and shows a dose-dependent inhibition of proliferation, as seen in FIGS. 22-24. The $IC_{50}$ for all three pancreatic cancer cell lines was 20-25 µM at 24 hours. HPDE 6C7 cells were also treated with increasing concentrations of δ-tocotrienol for 24 hours, but were relatively resistant to the antiproliferative effects of tocotrienol, even at the highest concentrations, as seen in FIG. 25 taken at 24 hours after δ-tocotrienol treatment.

Figure 26:
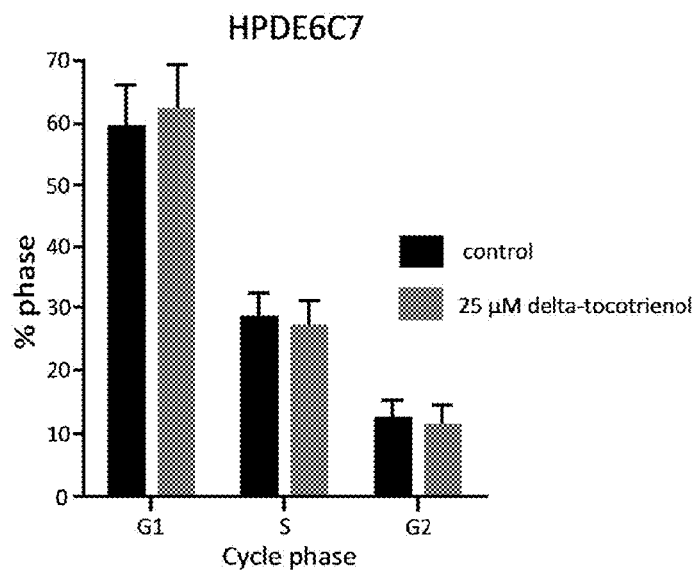
FIG. 26 is a graph showing significant G1 cell cycle arrest in HPDE 6C7 pancreatic cancer cell lines treated with δ-tocotrienol (25 μM). In contrast, δ-tocotrienol had no effect on cell cycle phase in immortalized human pancreatic ductal epithelial cells (HPDE 6C7).
Figure 27:
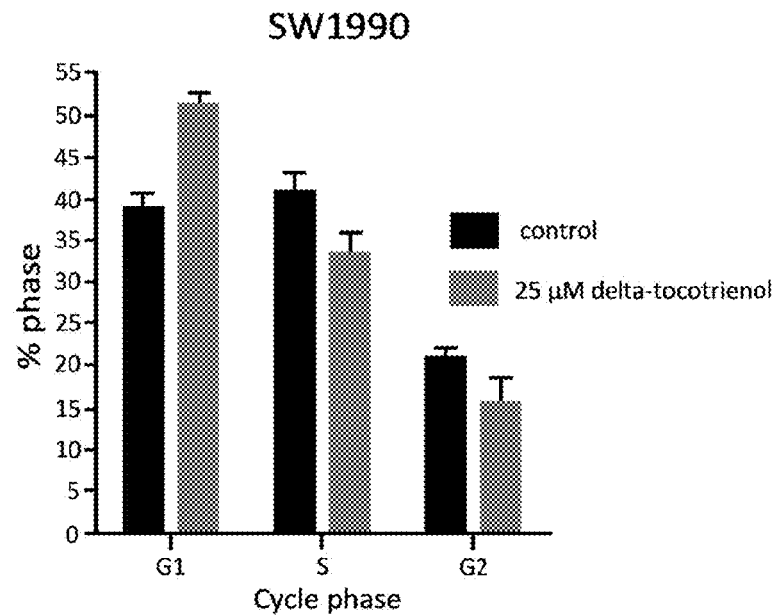
FIG. 27 is a graph showing significant G1 cell cycle arrest in SW1990 pancreatic cancer cell lines treated with δ-tocotrienol (25 μM). In contrast, δ-tocotrienol had no effect on cell cycle phase in immortalized human pancreatic ductal epithelial cells (HPDE 6C7).
Figure 28:
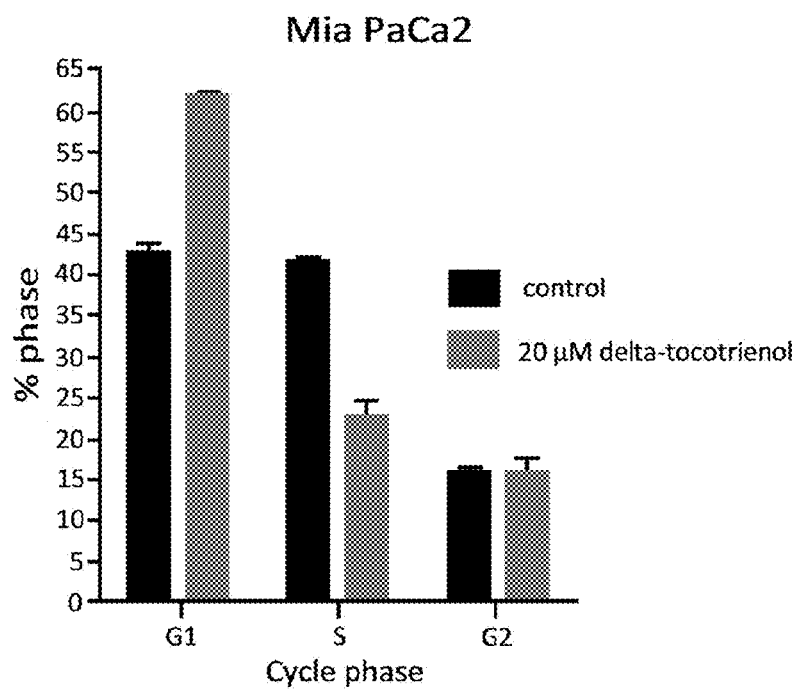
FIG. 28 is a graph showing significant G1 cell cycle arrest in MiaPaCa2 pancreatic cancer cell lines treated with δ-tocotrienol (20 μM). In contrast, δ-tocotrienol had no effect on cell cycle phase in immortalized human pancreatic ductal epithelial cells (HPDE 6C7).
Figure 29:
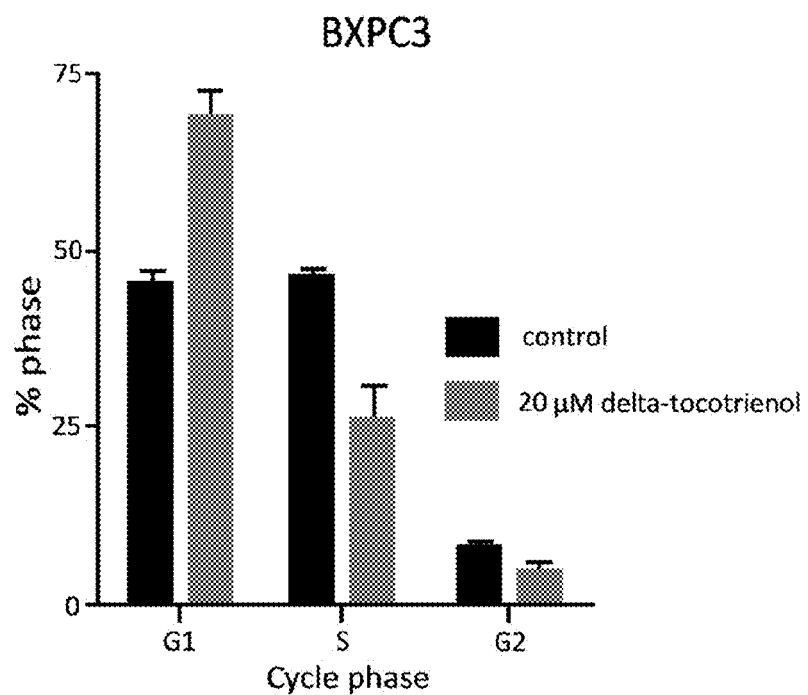
FIG. 29 is a graph showing significant G1 cell cycle arrest in BXPC3 pancreatic cancer cell lines treated with δ-tocotrienol (20 μM). In contrast, δ-tocotrienol had no effect on cell cycle phase in immortalized human pancreatic ductal epithelial cells (HPDE 6C7).
Figure 30A:
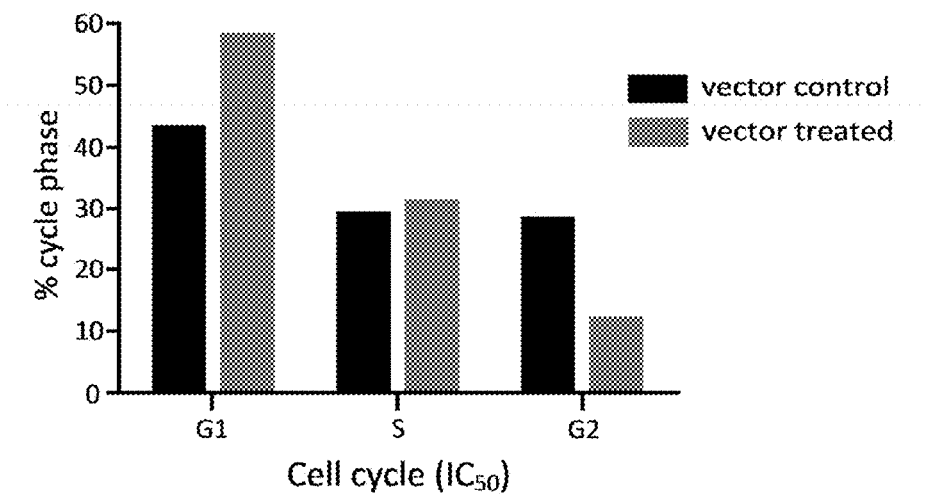
FIGS. 30A and B are graphs showing that siRNAp27 rescues tocotrienol induced G1-S cell cycle arrest in pancreatic cancer cells. A. Cell cycle analysis of vector-treated cells. B. Cell cycle analysis of siRNAp27-treated cells.
Figure 30B:
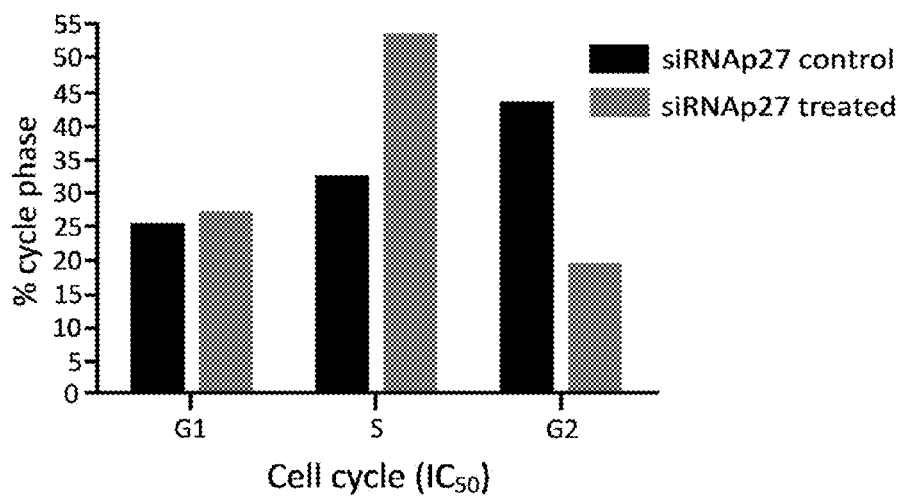

MIA PaCa2, SW 1990, BXPC3 and HPDE 6C7 cells were treated with either δ-tocotrienol 20 µM or vehicle for 24 hours. Cells were harvested, washed twice in PBS, and fixed in ethanol overnight. Pellets were washed the following day in PBS, stained with propidium iodide, and analyzed by flow cytometry for cell cycle phase. Results show that δ-tocotrienol causes selective G1 cell cycle arrest and is associated with upregulation of the cyclin kinase inhibitor p27$^{kip1}$, as seen in FIGS. 26 and 27, which show significant G1 cell cycle arrest in all three pancreatic cancer cell lines treated with δ-tocotrienol. In contrast, δ-tocotrienol had no effect on cell cycle phase in immortalized human pancreatic ductal epithelial cells (HPDE 6C7). Important regulators of the G1 cell cycle phase include members of the cyclin kinase inhibitor family. One of these members, $p27^{kip1}$, appears to be important in the progression of pancreatic cancer. FIGS. 30A and B shows that siRNAp27 rescues tocotrienol induced G1-S cell cycle arrest in pancreatic cancer cells.

Figure 31:
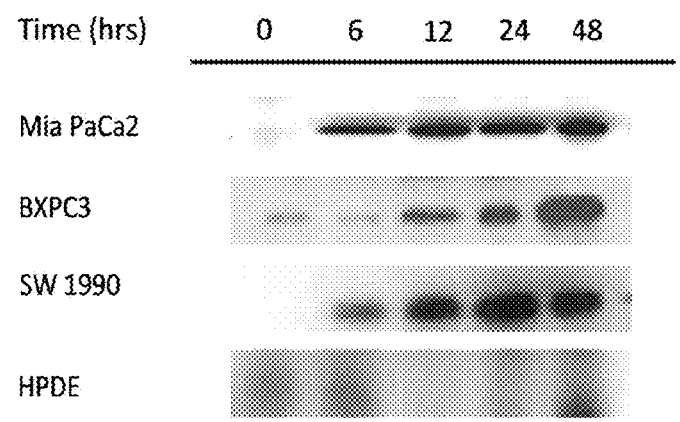
FIG. 31 is a series of blots showing a time dependent upregulation in $p27^{kip1}$ expression in all four pancreatic cancer cell lines. In contrast, a downregulation of $p27^{kip1}$ is seen in HPDE 6C7 cells treated with δ-tocotrienol.

Cell cycle inhibition by δ-tocotrienol was associated with altered protein expression of $p27^{kip1}$. The same 4 cell lines were treated with δ-tocotrienol (20 µM) and collected at progressive time intervals. Whole cell lysates were made from cell pellets washed twice in PBS and lysed in M-PER (Mammalian Protein Extraction Reagent, Pierce). Proteins from lysates were separated by SDS-PAGE and immunoblotted for $p27^{kip1}$ (BD Biosciences). FIG. 31 shows a time dependent upregulation in $p27^{kip1}$ expression in all three pancreatic cancer cell lines. In contrast, a downregulation of $p27^{kip1}$ is seen in HPDE 6C7 cells treated with 8-tocotrienol.

Figure 32:
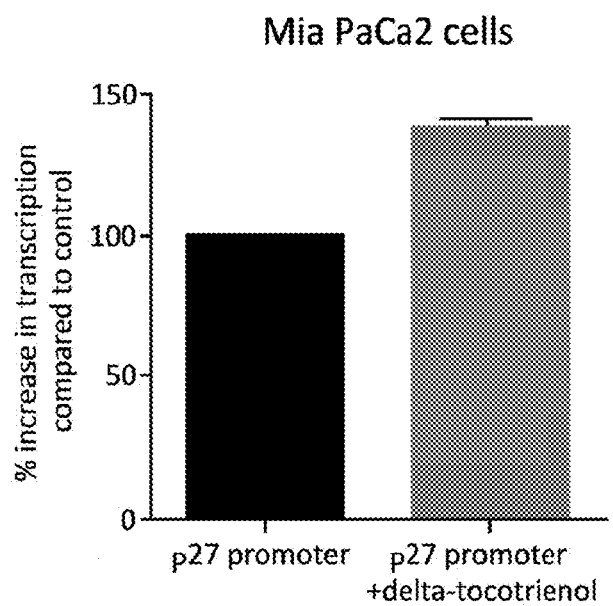
FIG. 32 is a graph showing an increase in luciferase activity in MIA PaCa2 cells treated with δ-tocotrienol.
Figure 33A:
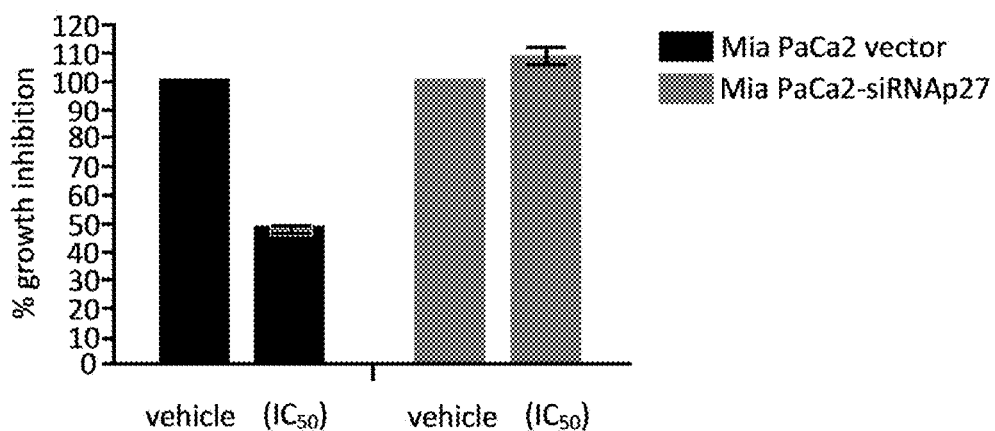
FIGS. 33A and B are a graph and associated blots showing siRNAp27 rescues tocotrienol inhibition of pancreatic cancer cell growth. A. A graph showing MiaPaCa2 cells treated with vector only or siRNAp27. B. A blot showing p27 and beta-actin for the vector or siRNA.
Figure 33B:
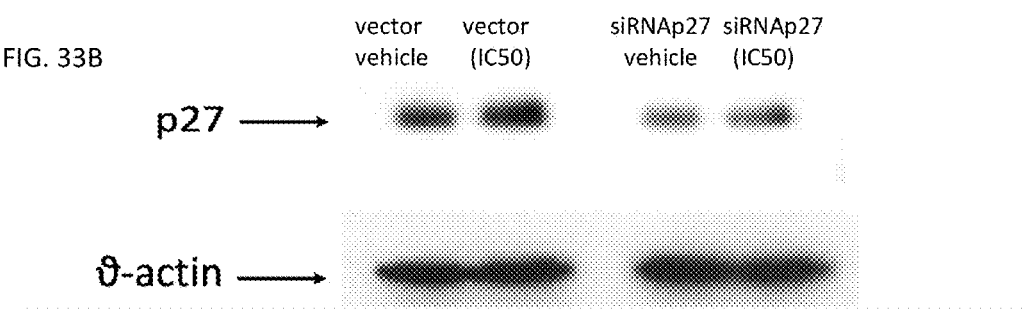

The mechanism by which δ-tocotrienol upregulates $p27^{kip1}$ protein expression was investigated using a luciferase reporter assay. Mia PaCa2 cells transfected with a $p27^{kip1}$ luciferase reporter (Wang, et al. Activation of p27Kip1 Expression by E2F1. A negative feedback mechanism. J Biol. Chem. 2005 Apr. 1; 280(13):12339-43. Epub 2005 Feb. 14) were treated with either δ-tocotrienol (20 µM) or vehicle for 24 hours and luciferase activity was then measured using a luminometer. MIA PaCa2 cells treated with δ-tocotrienol showed an increase in luciferase activity, as seen in FIG. 32, suggesting δ-tocotrienol increases $p27^{kip1}$ protein expression through transcriptional upregulation. This dynamic is further demonstrated by the rescue of tocotrienol inhibition of MiaPaCa-2 cells by siRNAp27, seen in FIGS. 33A and B.

Figure 34:
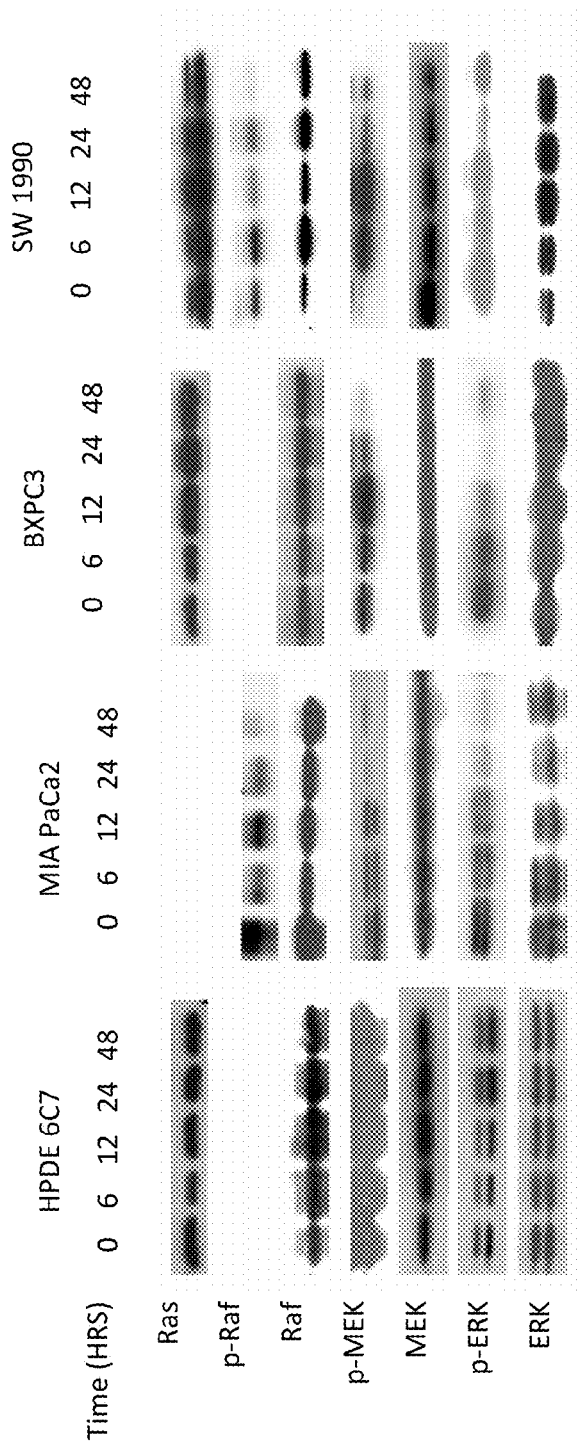
FIG. 34 is a blot series showing selective inhibition by δ-tocotrienol of the downstream phosphorylated targets of oncogenic Ras p-cRaf, p-MEK, and p-ERK. HPDE 6C7 cells were resistant to the inhibitory effects of δ-tocotrienol.
Figure 35:
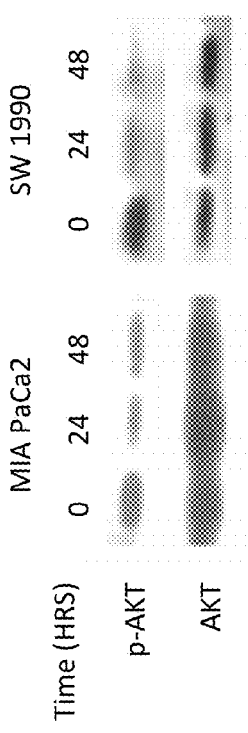
FIG. 35 is a blot series showing MIA PaCa2 and SW1990 cells treated with δ-tocotrienol (20 μM) for 24 and 48 hours. Cell lysates were run by SDS-PAGE and immunoblotted for p-AKT and AKT (Cell Signaling). The blots show a decrease in p-AKT protein levels, but not AKT at 24 and 48 hours.
Figure 36A:
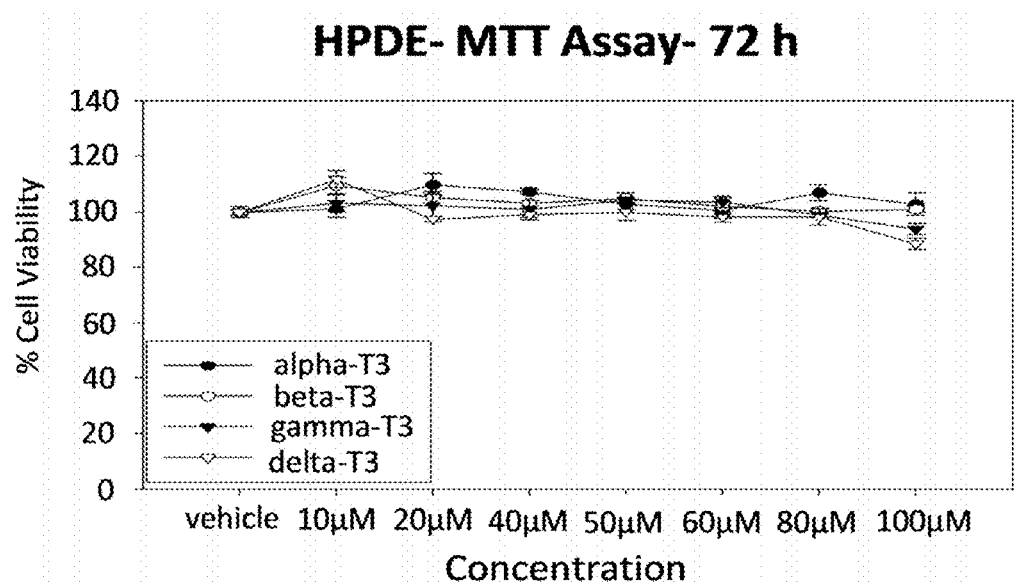
FIGS. 36A and B are graphs showing the effect of tocotrienols on Human Pancreatic Ductal Epithelial Kras Transformed cells (MTT). (A) Tocotrienols (10-100 μM) had no effect on the proliferation of normal immortalized human pancreatic ductal epithelial cells at 72 hours. (B) However, β-, γ-, and δ-tocotrienol significantly inhibited human pancreatic ductal epithelial cells transformed with oncogenic K-ras. δ-Tocotrienol was the most bioactive tocotrienol while α-tocotrienol had no effect. Points, means; bars, SE (n=3). *p<0.001 vs. vehicle. # p<0.02 vs. vehicle
Figure 36B:
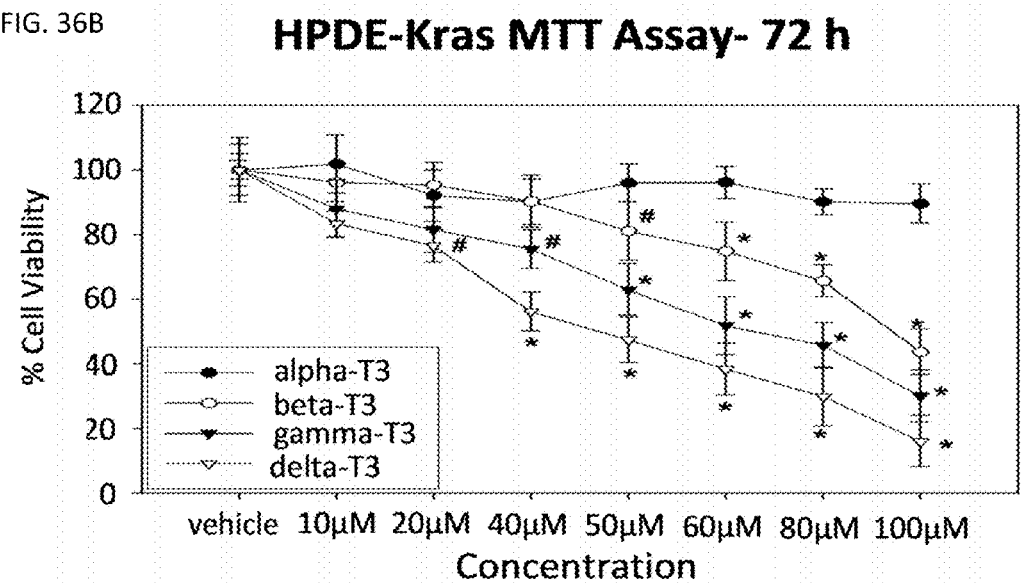

More than 80% of pancreatic cancers demonstrate abnormal oncogenic Ras signaling. The Ras effector pathways Raf-MEK-ERK and PI3 kinase-AKT are important for cell proliferation and survival, respectively. Pancreatic cancer cell lines (MIA PaCa2, SW1990, BXPC3) and HPDE 6C7 cells were treated with 8-tocotrienol (20 µM) and cell lysates were collected and prepared at progressive time intervals as described above. Proteins from lysates were run by SDS PAGE and immunoblotted with the following antibodies: Ras, p-cRaf (ser 338), p-MEK1/2, MEK1/2, pERK 44/42, ERK 44/42 (Cell Signaling) and c-Raf (BD Transduction Laboratories). Treatment with δ-tocotrienol selectively inhibited downstream phosphorylated targets of oncogenic Ras p-cRaf, p-MEK, and p-ERK, as seen in FIG. 34. The MIA PaCa2 and SW1990 cells were then tested for AKT inhibition. The cells were treated with δ-tocotrienol (20 µM) for 24 and 48 hours and cell lysates were run by SDS-PAGE and immunoblotted for p-AKT and AKT (Cell Signaling). Treatment with δ-tocotrienol showed a decrease in p-AKT protein levels, but not AKT at 24 and 48 hours, as seen in FIG. 35. Taken together, the inhibition of downstream effectors of oncogenic Ras signaling by δ-tocotrienol without an effect on Ras protein levels may indicate a negative regulatory role of 8-tocotrienol on the function of oncogenic Ras. The pancreatic ductal epithelial cell proliferative inhibition by δ-tocotrienol was tested to see if it occurs through blocking aberrant signal transduction cascades. Immortalized human pancreatic ductal epithelial cells (HPDE) and human pancreatic ductal epithelial cells that were transformed by stable transfection of a mutated K-ras oncogene (HPDE-K-ras) were used to test the effect of tocotrienols on the proliferation of HPDE and HPDE-K-ras. While the tocotrienols did not affect normal human pancreatic ductal epithelial cells, δ-tocotrienol significantly inhibited human pancreatic ductal epithelial cells transformed with K-ras and was the most effective tocotrienol in inhibiting the proliferation of these cells, as shown in FIGS. 36A and B. By contrast, immortalized HPDE 6C7 cells were resistant to the inhibitory effects of δ-tocotrienol. Thus, 8-tocotrienol shows selective chemoprevention against oncogenic or potentially oncogenic cells.

Figure 37:
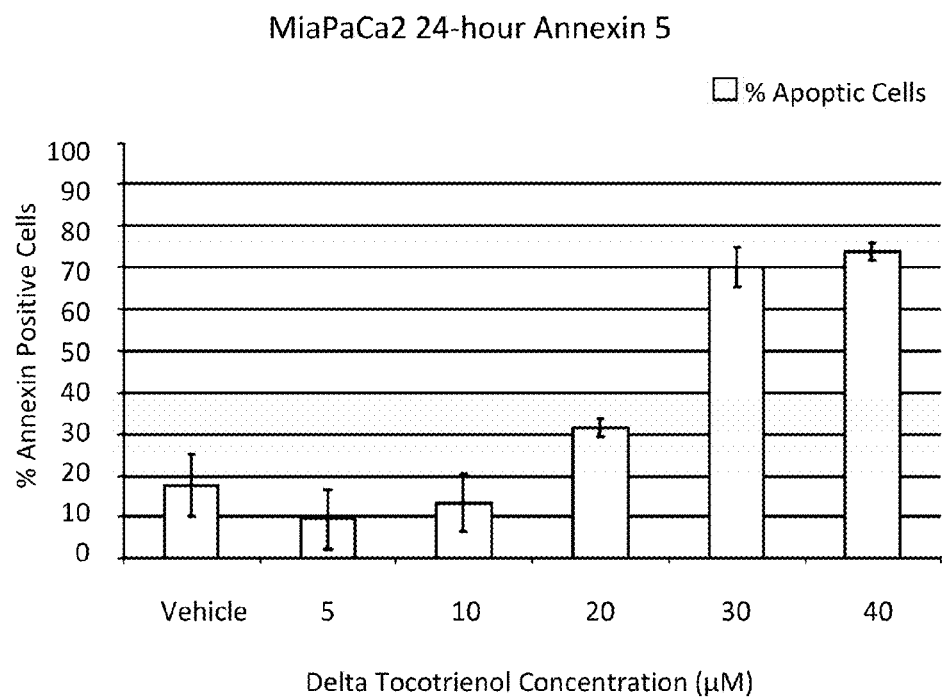
FIG. 37 is a graph showing activation of the caspase cascade as evidenced by cleavage of Caspase 8, Caspase 3, and Parp in a time dependent manner.

In addition to its chemopreventive effects, δ-Tocotrienol induces apoptosis in pancreatic cancer. MIA PaCa2 cells were treated with either δ-tocotrienol or vehicle for 24 hours. Cells were collected and stained with annexin V-FITC and analyzed by flow cytometry for apoptosis. A dose-dependent induction of early apoptosis was seen in MIA PaCa2 cells treated with δ-tocotrienol, as seen in FIG. 37. MIA PaCa2 cells and HPDE 6C7 cells were treated with vehicle or δ-tocotrienol (20 µM) for 24 hours, then harvested and stained for TUNEL. MIA PaCa2 cells treated with δ-tocotrienol showed significant staining for TUNEL compared to vehicle or treated HPDE 6C7 cells, suggests selective induction of apoptosis in pancreatic cancer cells, as seen in FIG. 2. Cell lysates were prepared from MIA PaCa2 cells treated with 8-tocotrienol (20 µM) at progressive time intervals and proteins from lysates were run by SDS PAGE and immunoblotted for biomarkers of apoptosis. FIG. 6 shows activation of the caspase cascade as evidenced by cleavage of caspase 8, caspase 3, and PARP in a time dependent manner. Interestingly, MIA PaCa2 cells treated with δ-tocotrienol had no significant effect on mitochondrial pro-apoptotic proteins as shown by a lack of cytochrome C release or cleavage of caspase 9. Thus, without being bound to any specific theory, induction of apoptosis by δ-tocotrienol in pancreatic cancer cells occurs through activation of the extrinsic apoptotic pathway.

Example 6

Figure 38A:
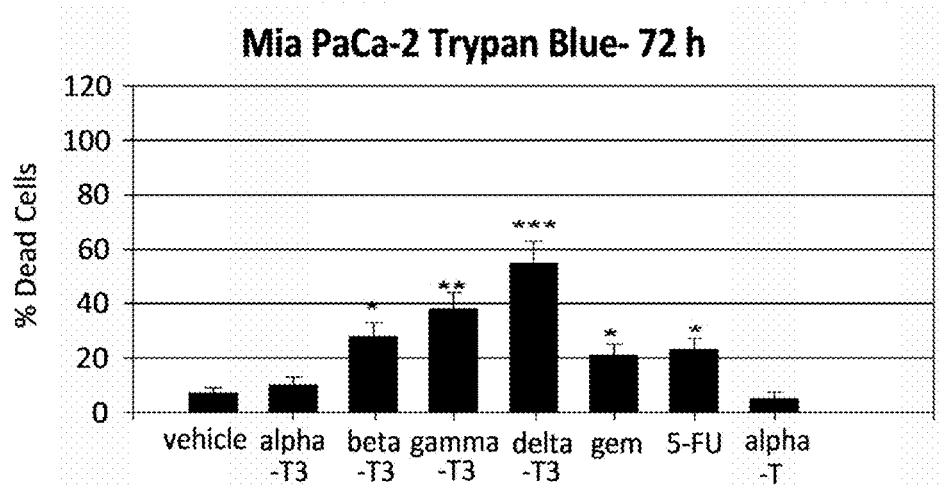
FIGS. 38A and B are graphs showing the effect of tocotrienols on pancreatic cancer survival (Trypan Blue and Cell death ELISA). The presence of 50 μM of δ-tocotrienol significantly induced the death (A) and apoptosis (B) of MiaPaCa2 pancreatic cancer cells at 72 hours, as compared with vehicle treated cells and cells treated with β-, or γ-tocotrienol as well as gemcitabine and 5-fluorouracil. In contrast, no effect was observed with α-tocopherol (alpha-T) or α-tocotrienol (alpha-T3) treated cells. bars, SE (n=3). *p<0.05 vs. vehicle. p<0.01 vs. vehicle. *p<0.001 vs. vehicle. T3=tocotrienol, T=tocopherol, vit E=vitamin E succinate, gem=gemcitabine, 5-FU=fluorouracil.
Figure 38B:
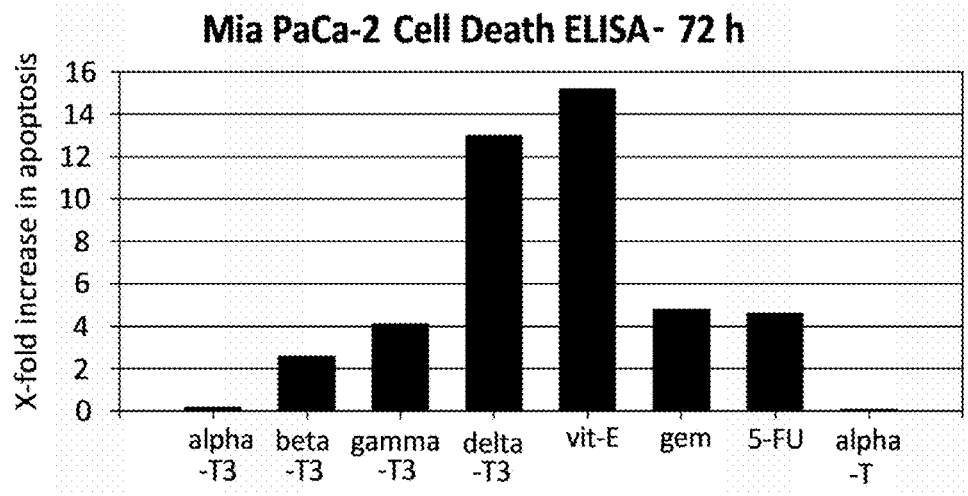

MIA PaCa2 cells ($3 \times 10^3$) were plated in 96 well plates and treated the following day with different compositions of tocoperhol, tocotrienol, gemcitabine, or fluorouracil. The cells were harvested 72 hours later and tested using trypan blue assay and cell death ELISA. The assays indicated that δ-tocotrienol was the most effective compound in inducing pancreatic cancer cell death and apoptosis as shown in FIGS. 38A and B, which correspond to the results seen in FIG. 11A.

Figure 39:
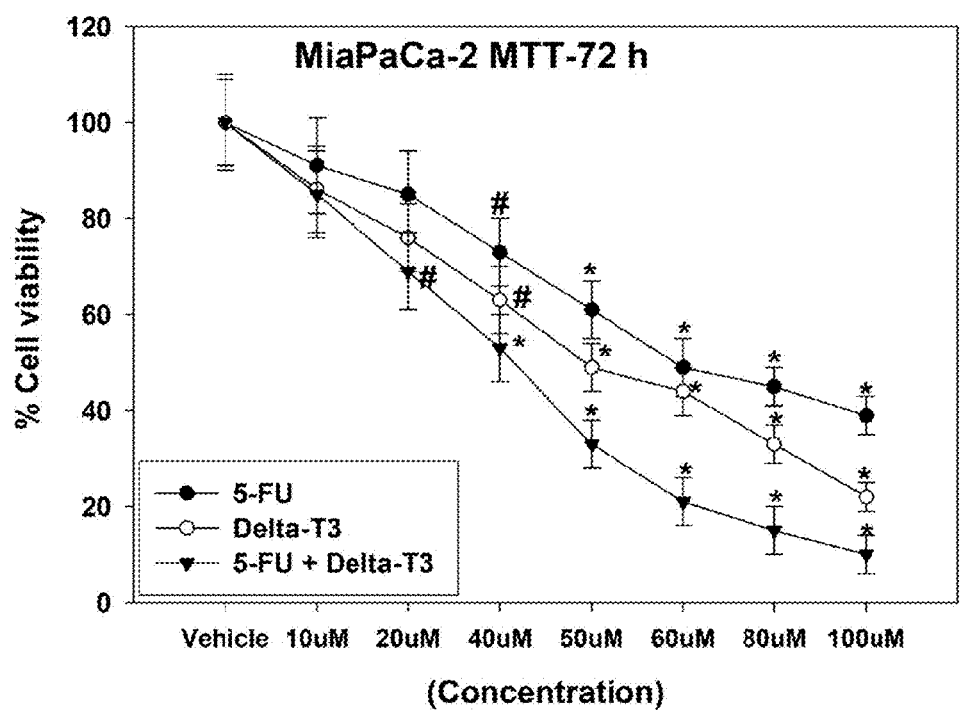
FIG. 39 is a graph MIA PaCa2 pancreatic cancer cells ($3\times10^3$) treated with indicated concentrations of delta-tocotrienol, fluorouracil (5FU), or a combination of the indicated delta-tocotrienol and 5FU. Proliferation was assessed by MTT at 72 hours after treatment and shows a dose dependent inhibition of proliferation. The $IC_{50}$ was 50 μM at 24 hours. *p<0.001 vs vehicle; # p<0.05 vs vehicle.
Figure 40:
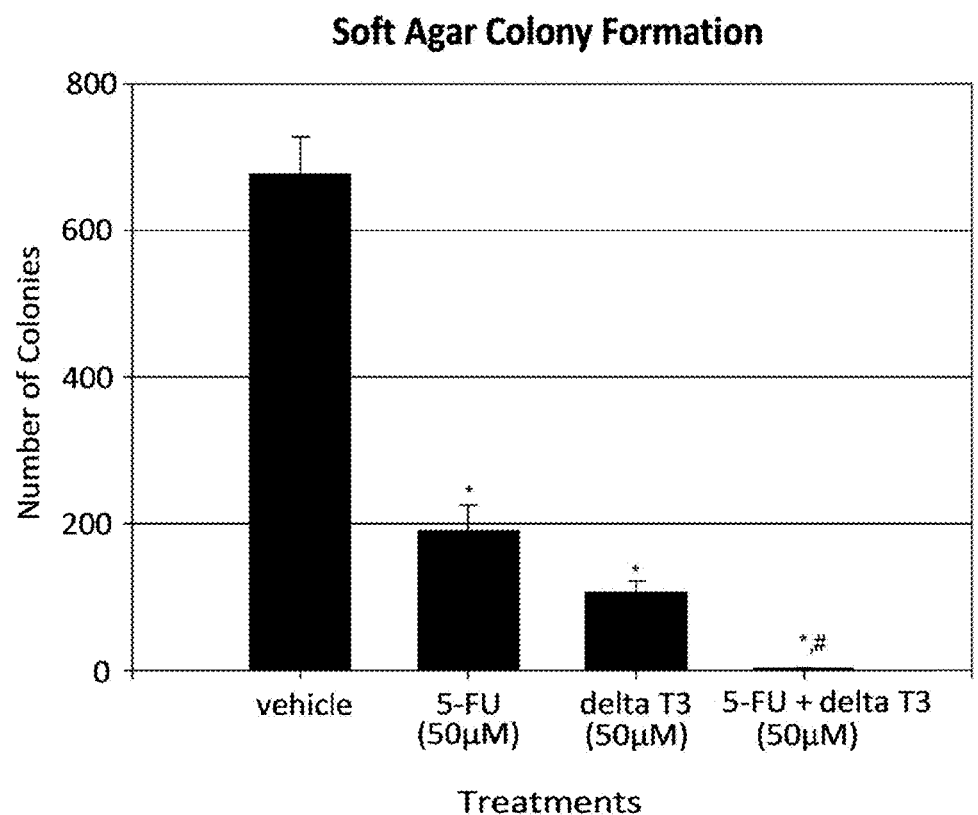
FIG. 40 is a graph showing MIA PaCa-2 cells treated with 50 μM delta-tocotrienol, 50 μM 5FU, or 50 μM delta-tocotrienol and 50 μM 5FU. Cells were then harvested after 24 hours, fixed, permeablized and stained with trypan blue. The graph shows a significant increase in apoptotic cells in vector compared to vehicle. a—p<0.001 vs vehicle; b—p<0.05 vs 5-FU; c—p<0.05 vs delta-tocotrienol; d—p<0.02 vs 5-FU.

The MiaPaCa 2 cells were plated as above into 96 well plates and treated the following day with increasing concentrations of δ-tocotrienol, fluorouracil (5FU), or a combination of δ-tocotrienol and fluorouracil. The cells were collected and analyzed for cell viability using an MTT assay. Increasing concentrations of 8-tocotrienol or 5FU showed enhanced cell death, which became significant at 50 µM for each, as seen in FIG. 39. By comparison, the combination treatment of 8-tocotrienol and fluorouracil further enhanced cell death, with significant inhibition of anchorage independent growth of MIA PaCa2 cells compared to vehicle at 40 µM. Moreover, the combination of 50 µM δ-tocotrienol and 50 µM 5-FU approximately a 10% lower viability level compared to δ-tocotrienol. At higher concentrations, the combination of δ-tocotrienol and 5-FU exhibited more disparity in cell viability compared to either δ-tocotrienol or 5-FU alone. The $IC_{50}$ for MIA PaCa2 was 50 µM at 24 hours. MIA PaCa2 cells ($3 \times 10^3$) were cultured as described in the Examples above, in 96-well plates and treated the following day with vehicle, δ-tocotrienol, fluorouracil, or a combination of δ-tocotrienol and fluorouracil. As seen in FIG. 40, both δ-tocotrienol and fluorouracil show significant inhibition of anchorage independent growth of MIA PaCa2 cells in soft agar when treated with weekly δ-tocotrienol compared to vehicle. Combination treatment with both δ-tocotrienol and fluorouracil exhibited further inhibition of growth, which was significantly reduced from either δ-tocotrienol or fluorouracil alone.

Figure 41:
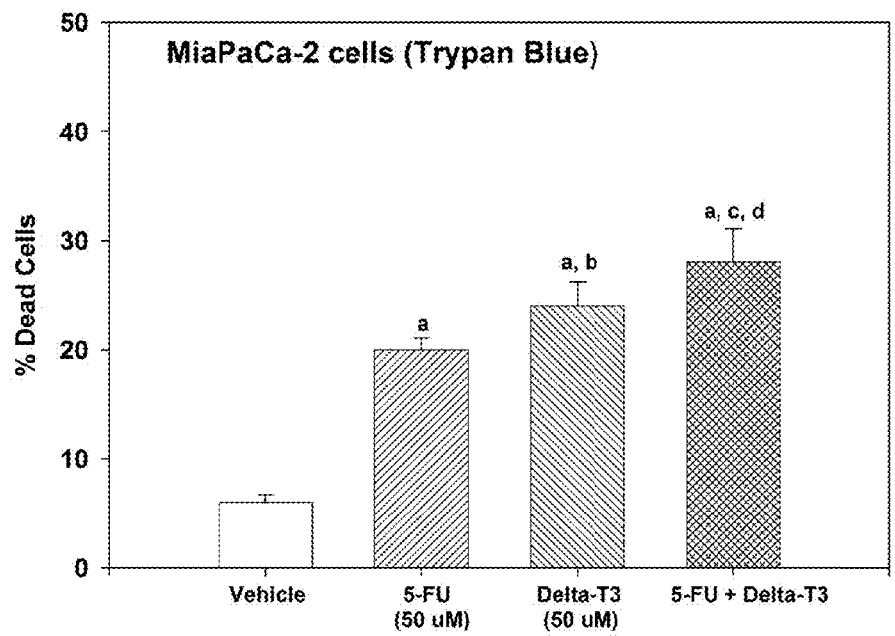
FIG. 41 are images showing saturated photoluminescent images of the accumulation of tocotrienol in mouse pancreas.
Figure 42:
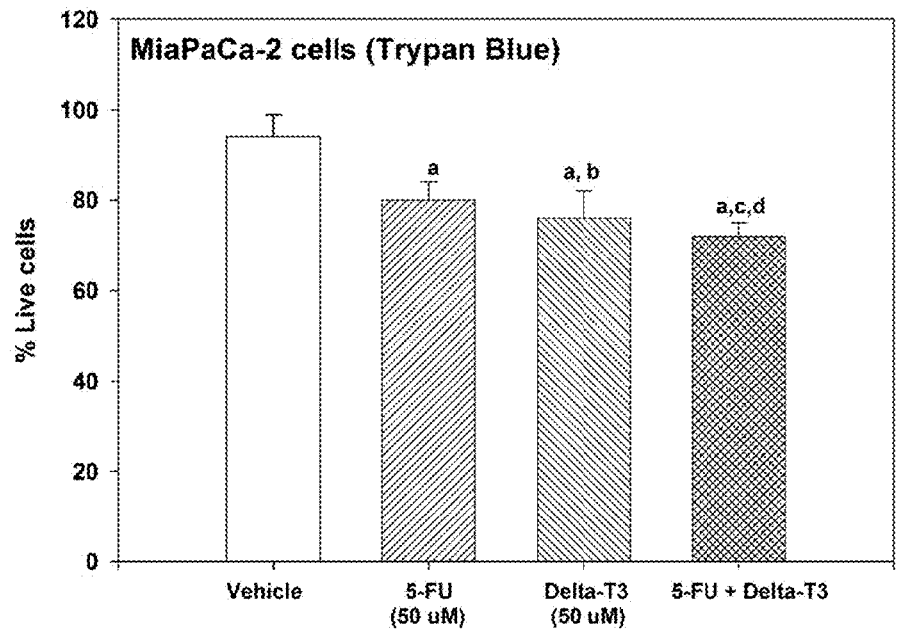
FIG. 42 is a graph showing the percentage of live MIA PaCa-2 cells 24 hours after treatment with 50 μM delta-tocotrienol, 50 μM 5FU, or 50 μM delta-tocotrienol and 50 μM 5FU. Cells were harvested, fixed, permeablized and stained with trypan blue. The graph shows a significant increase in apoptotic cells in vector compared to vehicle. a—p<0.01 vs vehicle; b—p<0.05 vs 5-FU; c—p<0.05 vs delta-tocotrienol; d—p<0.02 vs 5-FU.
Figure 43A:
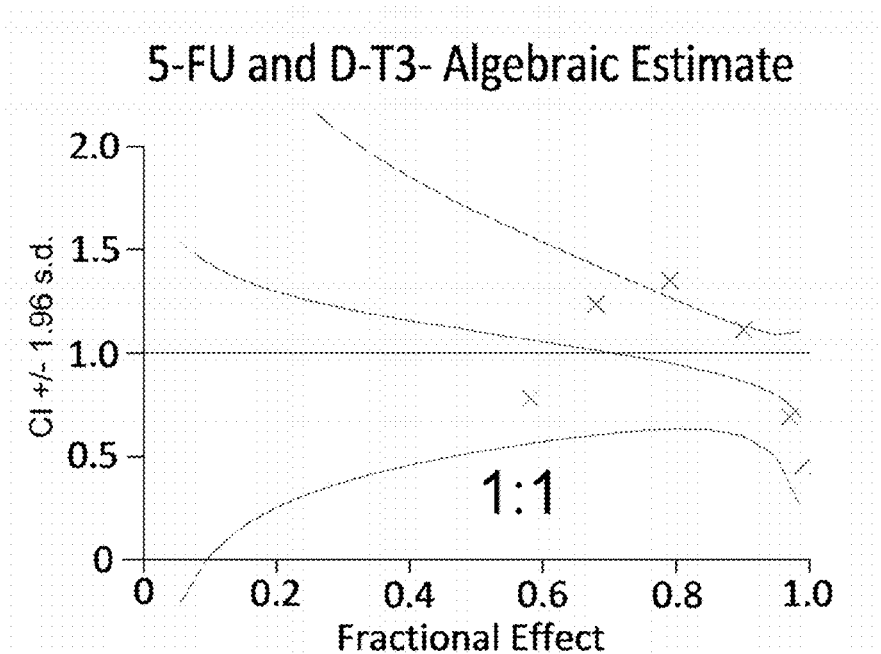
FIGS. 43A and B are graphs showing the cumulative index plots for fluorouracil and delta-tocotrienol at (A) 1:1 and (B) 1:2 ratio of fluorouracil to delta-tocotrienol.
Figure 43B:
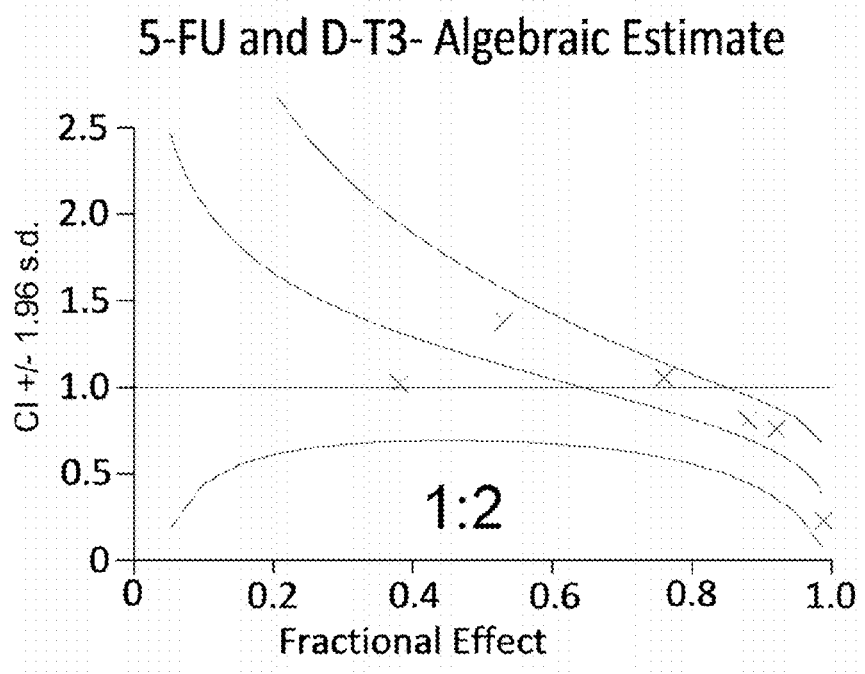

MIA PaCa-2 cells were treated vehicle or an anti-proliferative treatment comprising 50 μM δ-tocotrienol, 50 μM 5-FU, or 50 μM δ-tocotrienol and 50 μM 5-FU for 24 hours. Cells were harvested, fixed, permeablized and stained with trypan blue. As seen in FIGS. 41 and 42, treatment with 5-FU showed increased cell death, with δ-tocotrienol exhibiting further cell death, which is significantly more than 5-FU alone. The combination of δ-tocotrienol and 5-FU showed significantly enhanced cell death beyond either δ-tocotrienol or 5-FU alone, as seen in FIGS. 43A and B. The "combination index" (CI) depicts synergism (CI<1), additive effect (CI=1), and antagonism (CI>1) (Chou, Drug combination studies and their synergy quantification using the Chou-Talalay method. Cancer Res. 2010 Jan. 15; 70(2):440-6).

Example 7

Figure 44:
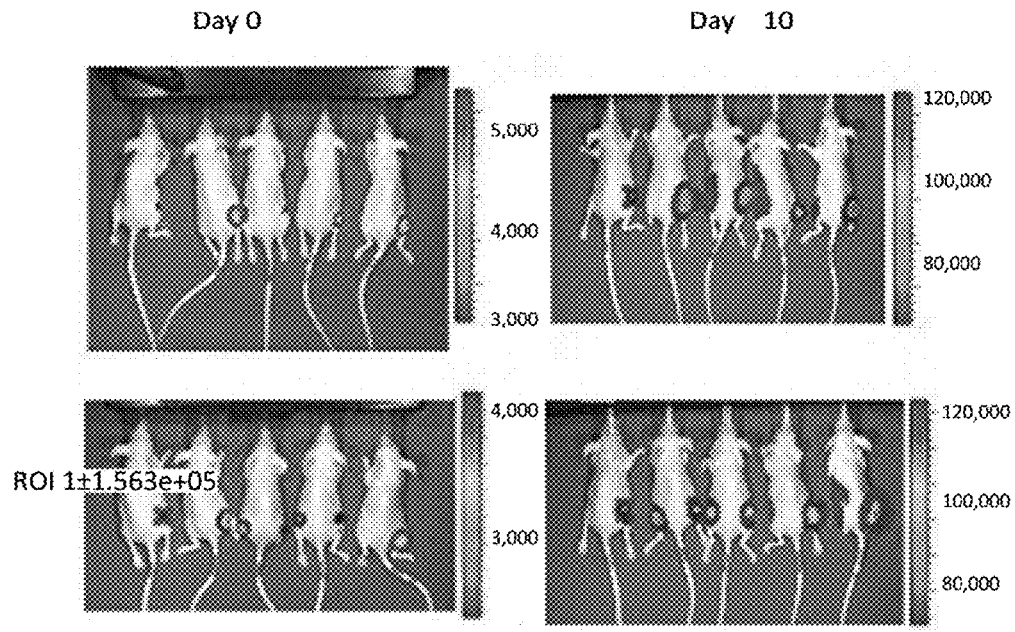
FIG. 44 shows representative luminescent measurements of control and δ-tocotrienol groups prior to treatment and at day 10. Rate of growth by day 10 of treatment is less in the tocotrienol treatment group. Stable transfectants of MIA PaCa2 cells with luciferase were injected subcutaneously into nude mice. Tumor volumes were measured every 2 days with calibers and the rate of growth was determined weekly by measuring tumor luminescence using the IVIS 100 Xenogen system. Tumors of similar volume (100-150 mm³) and rate of growth based on luminescence were randomized to receive either vehicle or δ-tocotrienol (100 mg/kg/day) by gavage for 20 days.
Figure 45:
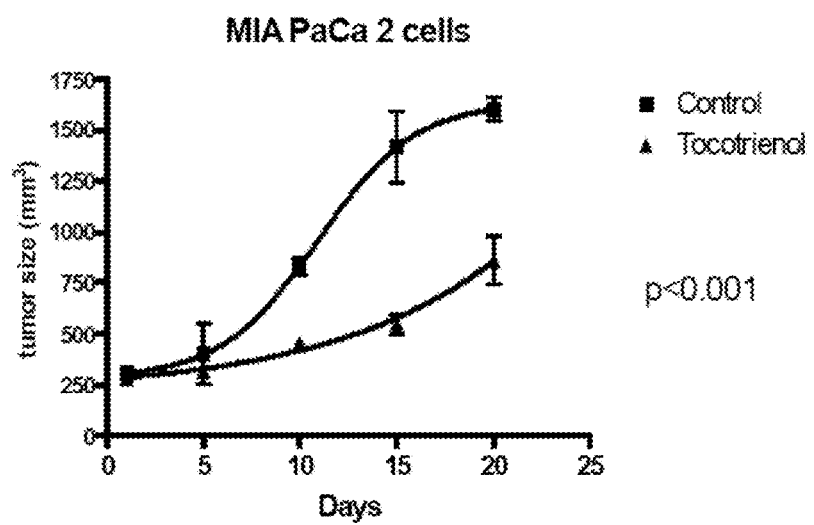
FIG. 45 is a graph showing significant reduction in tumor growth by 50% in xenografts treated with δ-tocotrienol compared to vehicle.
Figure 46:
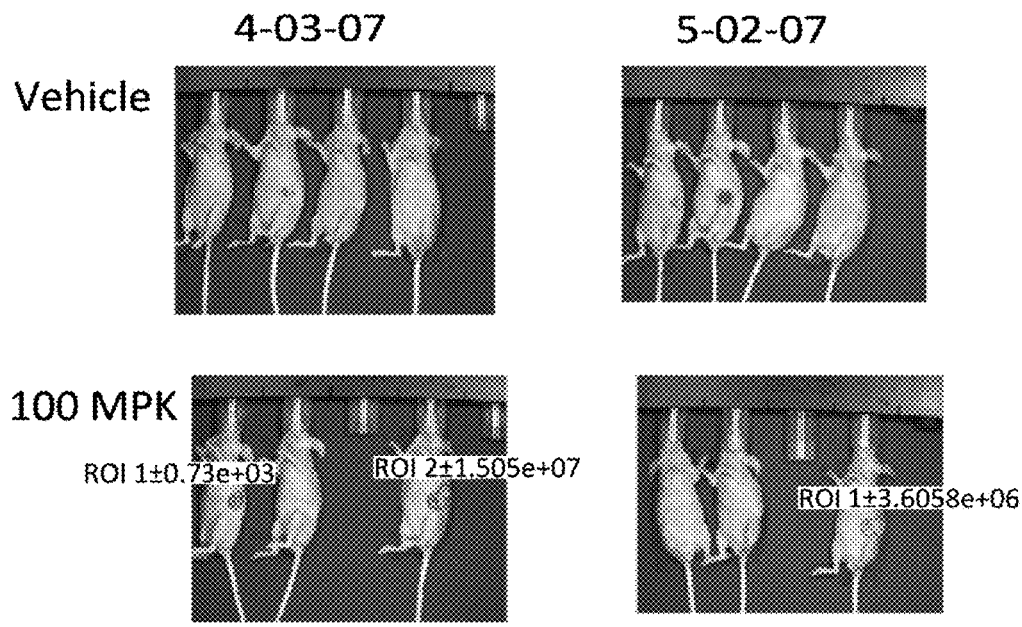
FIG. 46 are saturated luminescent images of in vivo results showing delta-tocotrienol inhibits pancreatic cancer metastasis. Images show comparison of vehicle vs. 100 MPK
Figure 47:
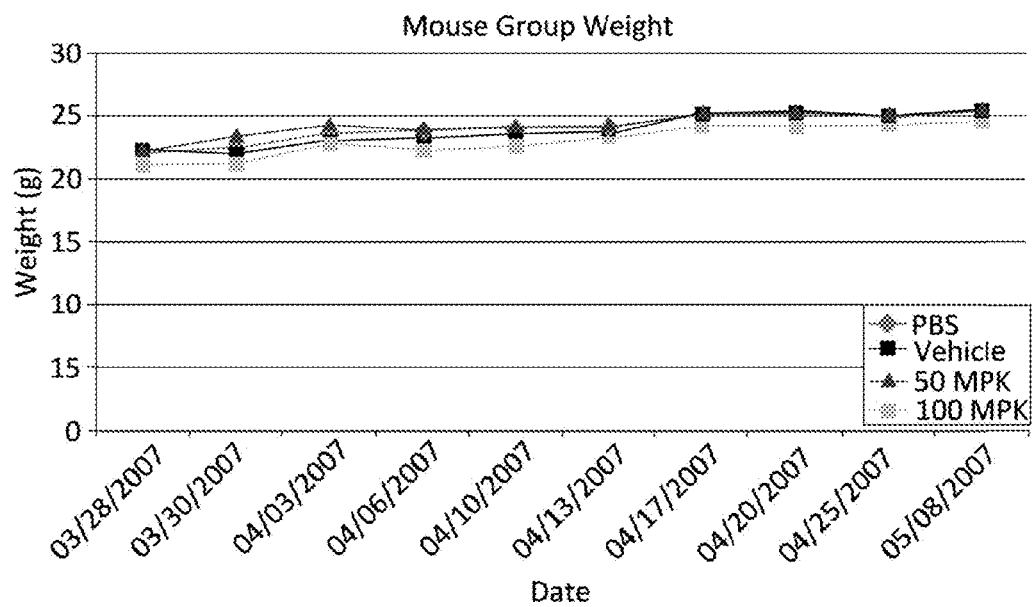
FIG. 47 is graph quantification of tumor metastasis by mouse weight group.

As treatment of pancreatic cancer cell lines with δ-tocotrienol resulted in induction of apoptosis in vitro, in vivo tests were used to confirm the results were applicable to treatment of a patient. Stable transfectants of MIA PaCa2 cells with luciferase were injected subcutaneously into nude mice. Mice were treated with either rice bran oil (vehicle) or δ-tocotrienol (100 mg/kg/day) via gavage five times per week. Tumor volumes were measured every 2 days with calibers and the rate of growth was determined weekly by measuring tumor luminescence using the IVIS 100 Xenogen system. Tumors of similar volume (100-150 mm$^3$) and rate of growth based on luminescence were randomized to receive either vehicle or δ-tocotrienol (100 mg/kg/day) by gavage for 20 days. Luminescent measurements of control and δ-tocotrienol groups prior to treatment and at day 10 show the rate of growth by day 10 of treatment is significantly less in the tocotrienol treatment group, as seen in FIG. 44. Tumor size measurements show a significant reduction in tumor growth by 50% in xenografts treated with δ-tocotrienol compared to vehicle, as seen in FIG. 45.

Additional testing showed δ-tocotrienol inhibits pancreatic cancer metastasis in a selective fashion, as shown in FIGS. 46-49, with tumor regression seen at the highest dose compared to vehicle/PBS. The apoptotic effect of delta-tocotrienol was selective for neoplastic cells as normal pancreatic cells and in vitro immortalized human pancreatic ductal epithelial cells were not sensitive to delta-tocotrienol.

Figure 50A:
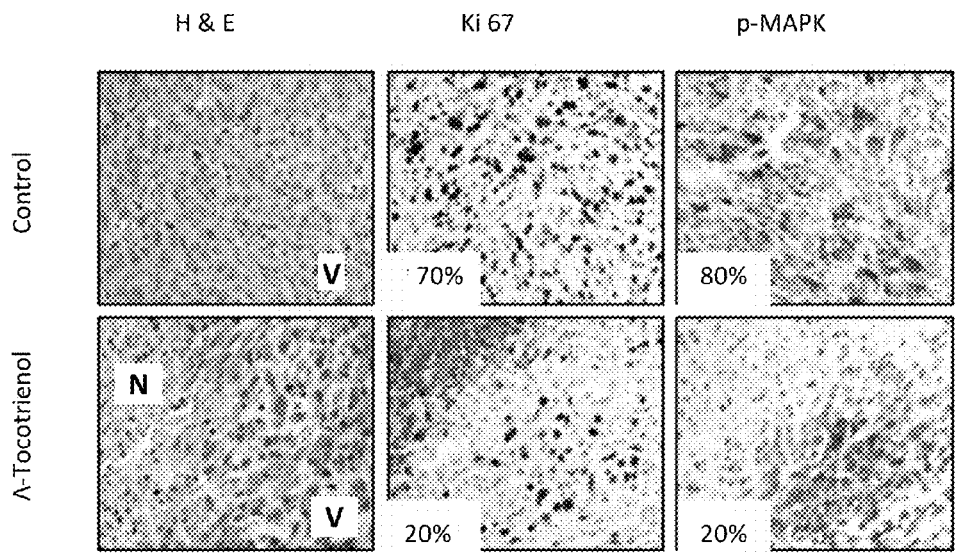
FIGS. 50A and B are immunohistochemical stains of the effects of δ-tocotrienol on oncogenic Ras signaling targets. Inhibition of proliferation is evidenced by a decrease in Ki67 and induction of apoptosis by TUNEL in tumors from mice treated with δ-tocotrienol as compared to tumors from the control group. A. A comparison of H&E, Ki67, and p-MAPK staining of control versus delta-tocotrienol treated MIA PaCA2 cells. B. A comparison of p-AKT, $p27^{kip1}$, and TUNEL staining of control versus delta-tocotrienol treated cells.
Figure 50B:
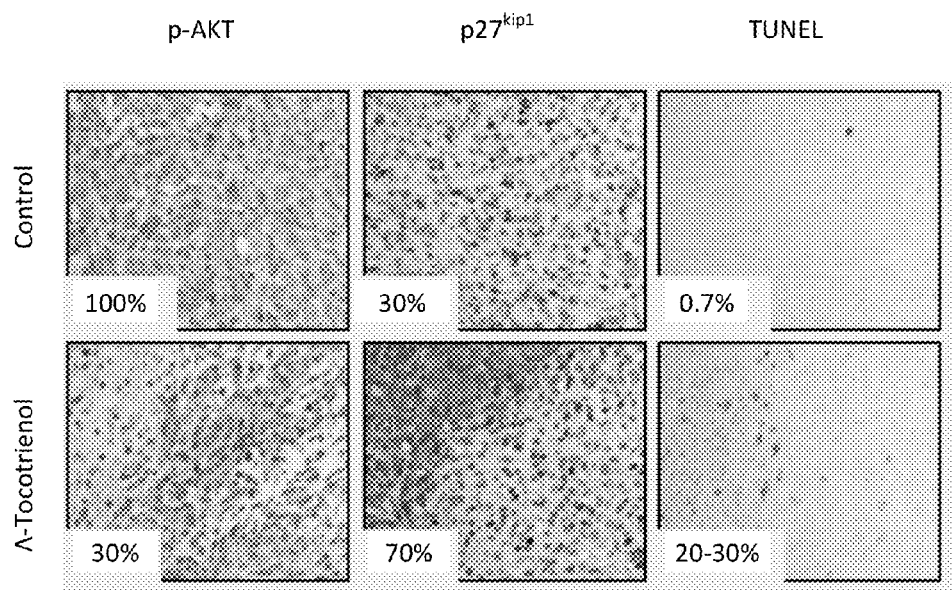
Figure 51:
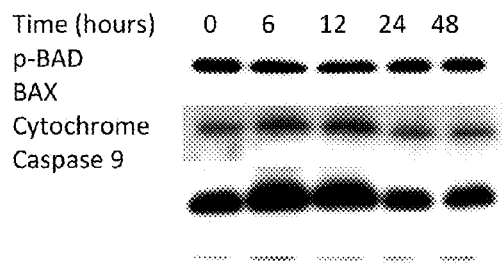
FIG. 51 is a series of blots showing activation of the apoptosis cascade as evidenced by caspase 9, cytochrome C, BAD and BAX in a time dependent manner.

Tumors were extracted on the last day of treatment and imbedded in paraffin. Immunohistochemical staining was performed to determine the effects of δ-tocotrienol on oncogenic Ras signaling targets. FIGS. 50A and B shows inhibition of proliferation as evidenced by a decrease in Ki67 and induction of apoptosis by TUNEL in tumors from mice treated with δ-tocotrienol as compared to tumors from the control group. Furthermore, the biomarker proteins p-MAPK and p-AKT were decreased and p27$^{kip1}$ expression was increased in δ-tocotrienol treated tumors. Further, Treatment of pancreatic cancer cell lines resulted in activation of the caspase cascade of the extrinsic pathway of apoptosis induction as evidenced by cleavage of Caspase 8 and Caspase 3 but not caspase 9. Further evidence of the lack of mitochondrial mediated apoptosis in delta-tocotrienol induced apoptosis of pancreatic cancer cells was demonstrated by the lack of cytochrome C release and the absence of delta-tocotrienol modulation of mitochondrial associated proteins such as Bcl-2 and BAD, as seen in FIG. 51. These in vivo findings demonstrate reproducible alterations in cell signaling proteins shown in vitro, above. Taken together, these findings show δ-Tocotrienol selectively induces apoptosis in pancreatic cancer cell via the extrinsic apoptotic pathway. δ-Tocotrienol selectively inhibits the PI3-K/AKT pathway and induces apoptosis in vivo and reduces phosphorylation levels of serine/threonine kinase Akt in vitro and in vivo. This is associated with inhibition of AKT signaling targets. Moreover, overexpression of myr AKT in Pancreatic Cancer cells rescues the effect δ-Tocotrienol induces apoptosis in vitro and in vivo. This suggests that tocotrienol induces apoptosis in pancreatic cancer through activation of the caspase 8 cascade and suppression of the Akt survival pathway and shows that this micronutrient is useful for pancreatic cancer chemoprevention and treatment in vivo.

Putative cancer chemoprevention in plasma and mouse tissue by HPLC-UV via vitamin E and delta-tocotrienol is shown in FIG. 52. Tocotrienol was detectable in plasma and was significantly concentrated in the pancreas. Surprisingly, tocotrienol localizes in the pancreas by a factor of 10 when compared to liver and pancreatic tumor levels. These results indicate the mechanism for tocotrienol action.

Example 8

Historically, the chemopreventive benefit of an agent could only be shown by a reduced cancer incidence or mortality. The use of reduced incidence or mortality as end points makes chemoprevention trials long, large, costly, and, hence impractical except for cancers that have high event rates. Indeed, the only reports of chemoprevention trials for pancreatic cancer have come from subset analysis of chemoprevention trials conducted for other indications. This approach has resulted in inconclusive observations of the value of agents such as α-tocopherol, β-carotene, aspirin, and non-steroidal anti-inflammatory drugs (NSAIDs).

Developing "early phase" clinical trial methodologies for chemopreventive agents akin to the phase I and phase II studies for traditional cancer therapeutics is an important research priority to advance chemopreventive drug development in pancreatic cancer. Ideally these studies should confirm not only the potential for chemoprevention, but also answer questions about optimal dose and schedule. In response to these challenges, several investigators have proposed and initiated studies that focus on candidate surrogate end point biomarkers (SEBs) of the target lesion pathophysiology rather than on long-term cancer prevention.

In SEB trials, reduction in tumor incidence is replaced with evidence for reversal of one or more elements of the neoplastic phenotype, such as abnormal proliferation, cell survival, or aberrant gene expression. Specifically, these strategies focus on the effect of agents on a significant precancerous lesion, intraepithelial neoplasia (IEN). Whereas IEN is a validated precancer in most epithelial tissues, mucinous cystic neoplasms (MCNs), intraductal papillary mucinous neoplasms (IPMNs), and pancreatic intraepithelial neoplasia (PanIN), are the best-characterized IENs in pancreatic tissue. The progress of these lesions to invasive carcinoma is well characterized and surgical removals of these lesions are already recommended medical practice for prevention of pancreatic cancer.

Although SEB studies are well established in the setting of IENs that do not require surgical intervention, such as leukoplakia of the oral mucosa or Barrett's esophagus, such studies are more difficult to conduct in premalignant lesions requiring immediate surgical intervention because the index lesion is removed and is not amenable to subsequent follow-up. However, the need for sequential procedures to diagnose and remove invasive and preinvasive pancreatic lesions, provides an opportunity for short-term SEB studies. An interval of two to four weeks is standard in most practices, hence offering a window within which a chemopreventive agent can be administered to evaluate the effects of the agent on SEB modulation. The experiments show the value of standard SEBs such as proliferation rate, apoptosis index, and the expression of proteins (discussed below) that are modulated by the early genetic changes in these lesions.

In one embodiment, the invention includes surrogate endpoint biomarkers that were prevelant in the surgical specimens of patients who have undergone resection of invasive ductal adenocarcinomas of the pancreas (IPMNs). Tocotrienol, such as δ-tocotrienol from annatto bean, demonstrated selectively inhibition in human pancreatic cancer cells. The data shows that δ-tocotrienol affects a number of molecular processes including induction of apoptosis and inhibition of tumor growth and that δ-tocotrienol inhibits oncogenic signal transduction pathways in pancreatic neoplastic cells. Specifically, δ-tocotrienol decreases phospho-Raf, phospho-MEK, phospho-ERK, and phospho-AKT levels in human pancreatic cancer cells. Furthermore, δ-tocotrienol induces the expression of growth inhibitory mediators such as $p27^{Kip1}$ and activates the apoptotic mediators caspase 8 and caspase 3.

Cases of resected pancreatic ductal carcinoma from 1986 to 2006 were collected from the Moffitt Cancer Center Tumor Registry and Pathology information system. Slides from each case were reviewed by a single pathologist for histological tumor type, grade, and presence of ductal precursor lesions. Histologic type and grade were assigned based on current W.H.O nomenclature. Pancreatic carcinoma precursor lesions, termed pancreatic intraepithelial neoplasia (PanIN) were graded Ia, Ib, 2, and 3 according to published criteria (Hruban, 2001). Based on slide review, 10 representative tissue blocks were selected from ten consecutive resection specimens. Preference was given to sections showing carcinoma, (preferably more than one grade of carcinoma), normeoplastic ducts, and precursor lesions. All cases were ductal adenocarcinoma, NOS, or well to poorly differentiated.

Figure 48:
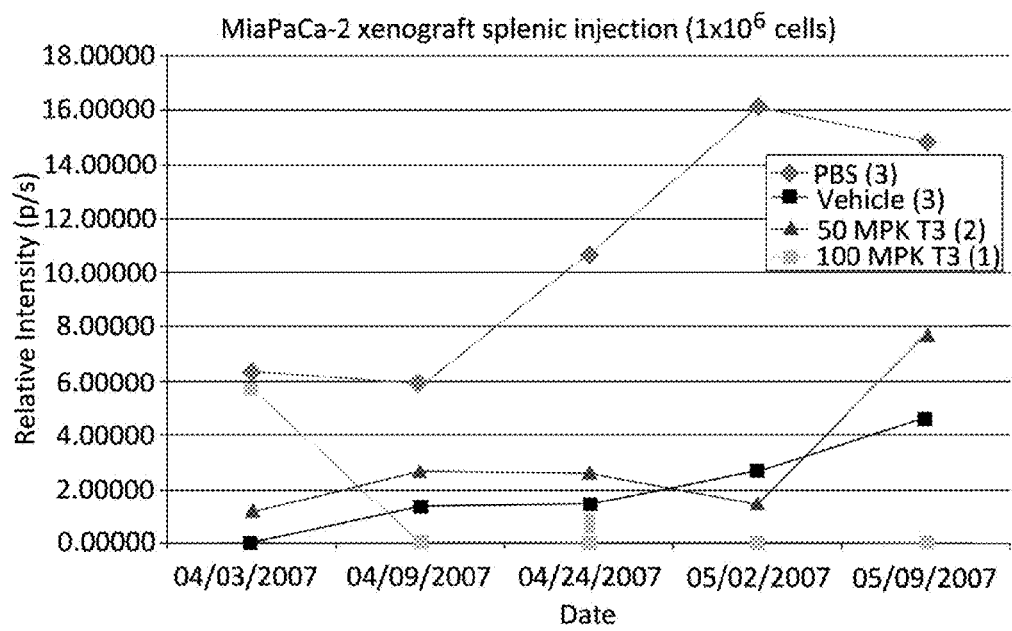
FIG. 48 is a graph showing the relative intensity (p/s)/time for PBS, vehicle, 50 MPK (T3), 100 MPK (T3).
Figure 49:
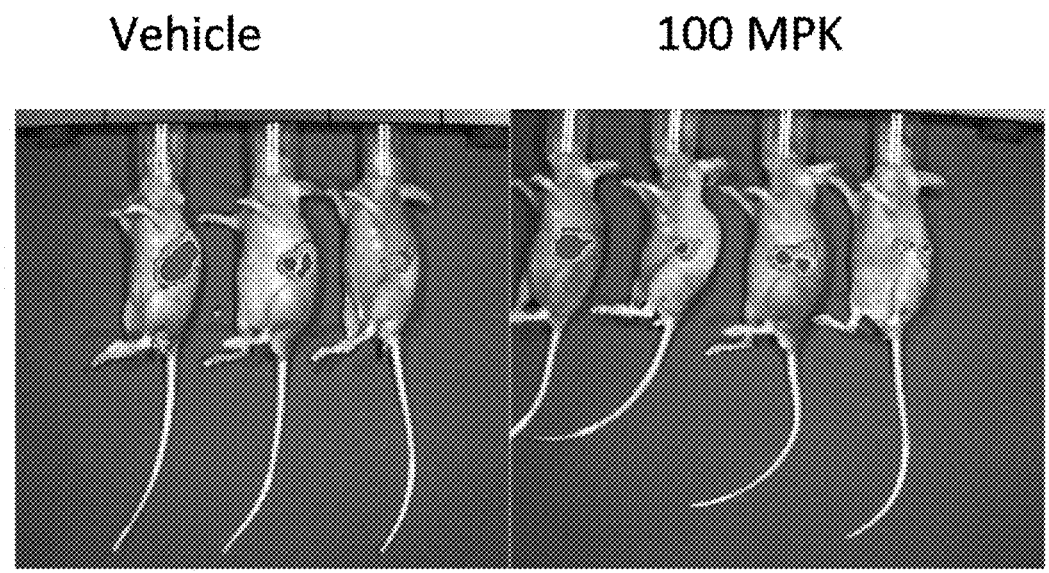
FIG. 49 saturated photoluminescent images of the accumulation of tocotrienol in mouse pancreas.
Figure 53A:
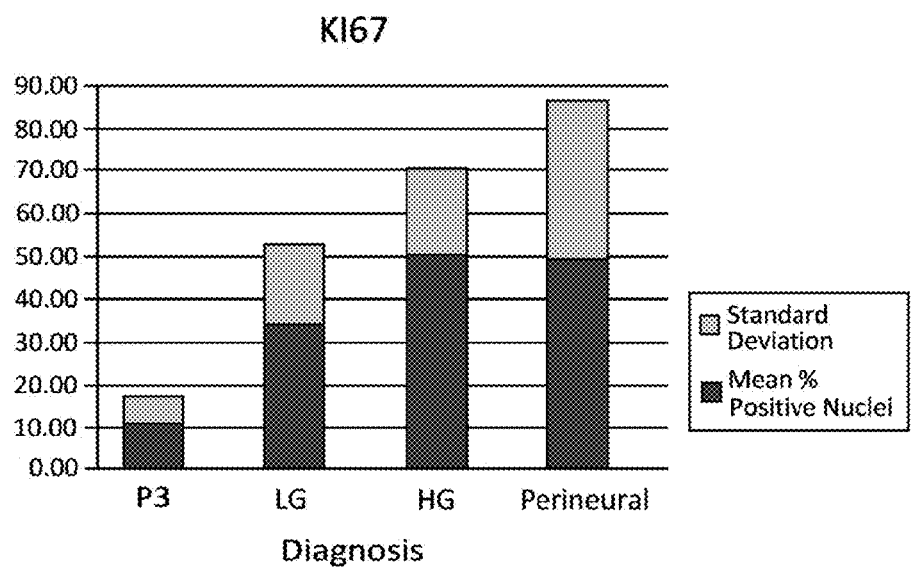
FIGS. 53A and B are graphs showing the proliferation of MIA PaCA2 cells based on the invasion and grade of tumor. A. An increase in proliferation rate as the degree of invasion and grade of tumor is increased is indicated by a progressive increase in the mean percentage of cells staining positive for Ki-67. B. A progressive decrease in the number of apoptotic cells stained with TUNEL, negatively correlating with the degree of tumor invasion.

The data shown in FIGS. 53A through 48 demonstrates the accuracy with which these intermediate biomarkers can be measured. Ki67 was noted to be a reliable marker of proliferation with progressive increase of a positive reaction in the nucleus from normal to intermediate to invasive carcinoma. An inverse progression was noted for TUNEL staining indicating oncogenic suppression of apoptosis in neoplastic pancreatic ductal cells. A similar inverse progression was observed in the expression of the p27 cyclin-dependent kinase inhibitor protein. In contrast, downstream mediators of activated oncogenic Ras signaling such as phospho-MAPK and phospho-AKT are increased. Remarkably, all patients with invasive ductal cancer of the pancreas and IPMNs had noninvasive precursor lesions in their surgical specimens.

No cases of undifferentiated carcinoma or ductal adenocarcinoma variants were selected for this pilot study. One section was cut from each block for routine Hematoxylin and eosin stains. Sections cut for immunohistochemistry were placed on poly-L-lysine coated slides. Antibodies used included Ki-67, p27, and p-MAPK. A TUNEL assay was used to evaluate for apoptosis Immunohistochemical studies were performed using standard immunohistochemical techniques. Slides were then scanned into the Ariol SL-50 (version 3.0.70) from Applied Imaging for accurate, reproducible, and objective high throughput analysis. Images were reviewed by one pathologist for representative areas of carcinoma, PanIN, reactive ducts, and non-neoplastic ducts. Well-differentiated and moderately differentiated carcinomas were grouped into one category of low grade for the purpose of this study. Poorly differentiated carcinoma was classified as high grade carcinoma. Additional areas of perineural invasion, if present on the slide, were also selected for analysis.

Figure 53B:
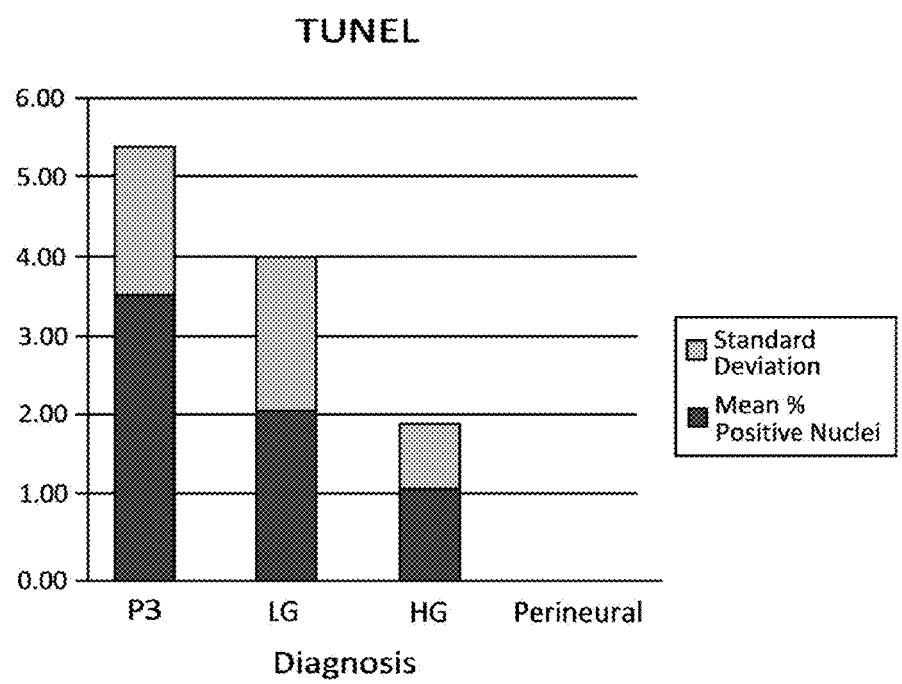

FIG. 53A shows an increase in proliferation rate as degree of invasion and grade of tumor is increased. This is indicated by a progressive increase in the mean percentage of cells staining positive for Ki-67. In contrast, FIG. 53B shows a progressive decrease in the number of apoptotic cells stained with TUNEL, negatively correlating with the degree of tumor invasion.

Figure 54:
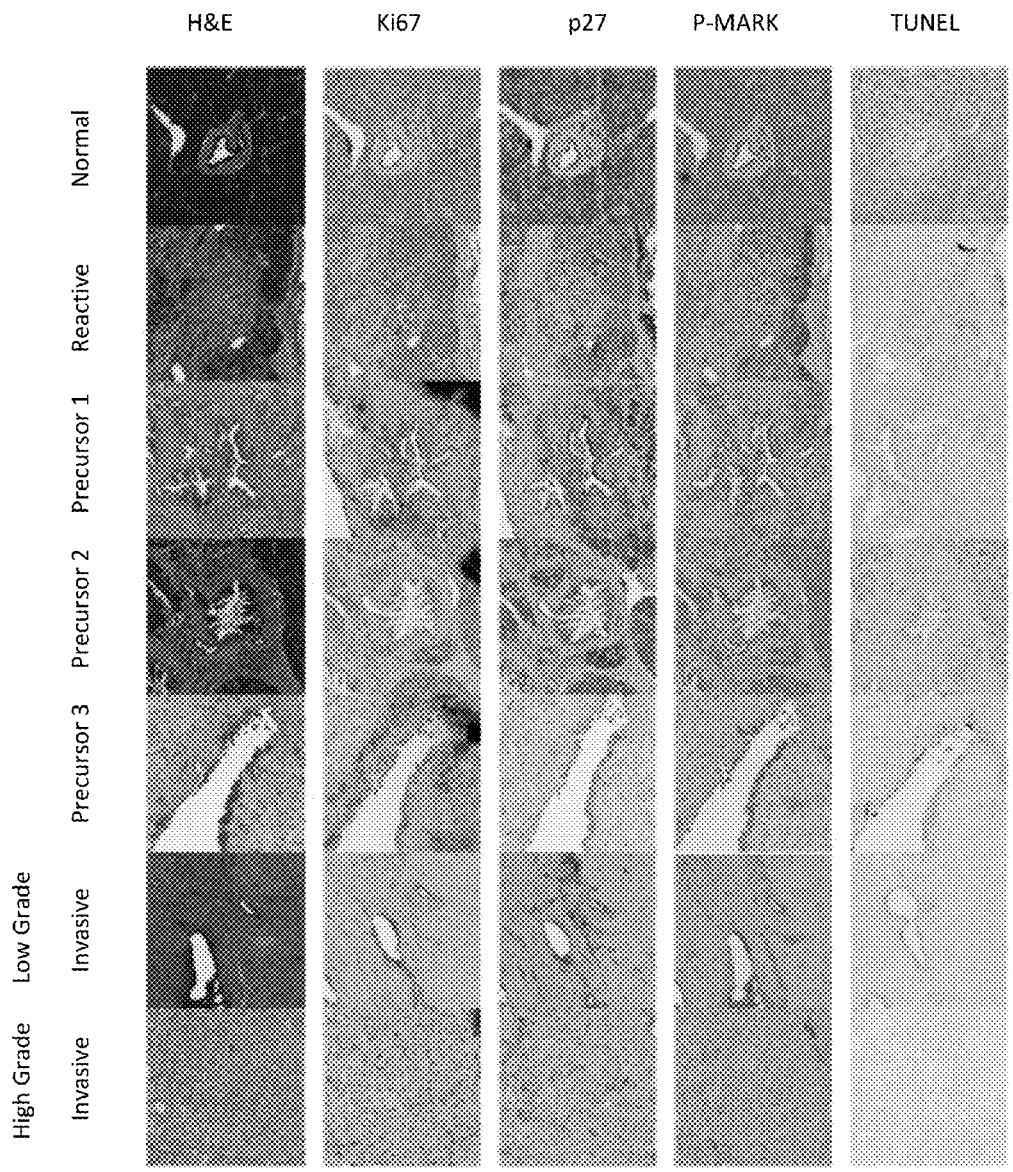
FIG. 54 is a series of representative slides of non-neoplastic pancreatic ductal tissue, reactive tissue, precursor lesions (PanIN 1-3), and low and high grade invasive carcinomas. Each representative area was stained with Hematoxylin and Eosin, and for Ki-67, p27, p-MAPK, and TUNEL. Results show an increase in Ki-67 and p-MAPK staining as pancreatic ducts progress from normeoplastic to PanIN to invasive carcinoma. The greatest degree of staining is in high grade tumors. In contrast p27 and TUNEL staining decrease with tumor invasiveness and progression. Indicating a loss of cell cycle inhibition and induction of apoptosis.

FIG. 54 shows representative slides of non-neoplastic pancreatic ductal tissue, reactive tissue, precursor lesions (PanIN 1-3), and low and high grade invasive carcinomas. Each representative area was stained with Hematoxylin and Eosin, and for Ki-67, p27, p-MAPK, and TUNEL.

Results show an increase in Ki-67 and p-MAPK staining as pancreatic ducts progress from non-neoplastic to PanIN to invasive carcinoma. The greatest degree of staining is in high grade tumors. In contrast p27 and TUNEL staining decrease with tumor invasiveness and progression. Indicating a loss of cell cycle inhibition and induction of apoptosis.

Another embodiment of the invention includes a method of screening for pancreatic ductal carcinoma, or a stage of pancreatic cancer in a subject by determining, such as in an isolated sample, the level of a biomarker; namely, p27. The level of the biomarker is then compared to a corresponding control level in one or more control samples. In a preferred embodiment the control samples are obtained from individuals who have been determined not to have pancreatic ductal carcinoma, or a stage of pancreatic cancer.

The determination of a statistically significant increase between the level of the biomarker in the subject and the level of the biomarker in the control sample(s) is indicative of the lack of pancreatic ductal carcinoma, or a stage of pancreatic cancer in the subject. A statistically significant decrease in the level of p27 in the subject, compared to the level of the biomarker in the control sample(s), indicates the presence of pancreatic ductal carcinoma, or a stage of pancreatic cancer in the subject.

In an alternate embodiment, the level of a second biomarker, namely Ki-67 and/or p-MAPK, is determined and compared to a control level of Ki-67 and/or p-MAPK in one or more control samples. A statistically significant increase between the level of Ki-67 and/or p-MAPK in the subject and the control sample(s) is indicative of pancreatic ductal carcinoma, or a stage of pancreatic cancer in the subject. A statistically significant decrease in the level of Ki-67 and/or p-MAPK in the subject, compared to the control sample(s), is indicative of the lack of pancreatic ductal carcinoma, or a stage of pancreatic cancer in the subject.

Methods of determining the level of the biomarker in the subject and control sample(s) are known to the ordinary practitioner. In one embodiment, as an example, the level of the biomarker is determined utilizing an antibody which binds the biomarker. The sample containing the biomarker is contacted with the antibody under conditions which allow binding of the biomarker to the antibody; the presence of the biomarker can then be quantified.

The invention also includes compositions useful in performing the associated methods. For example, the invention includes a composition comprising a plurality of isolated proteins which bind selectively to the protein products of the associated biomarkers; namely, Ki-67 and/or p-MAPK, and p27. In a preferred embodiment, the isolated proteins selectively amplify complementary double stranded DNA. A composition is also included comprising a plurality of biomarker specific primers, wherein each biomarker specific primer selectively amplifies double stranded DNA complementary to a unique biomarker such as Ki-67, p-MAPK and p27. Alternatively, the invention includes a composition comprising a plurality of isolated proteins which bind selectively to the protein products of at least two unique biomarkers, wherein each unique biomarker is selected from the group consisting of Ki-67, p-MAPK and p27.

Therefore, in one embodiment, the invention includes a method of determining the effectiveness of a chemotherapeutic agent by determining, in an isolated sample, a first level of a surrogate endpoint biomarker such as p27. The sample is then contacted with an experimentally effective amount of the chemotherapeutic agent being tested. After the chemotherapeutic agent has been administered, a second level of the surrogate endpoint biomarker is taken and compared to the first (pre-treatment) level. The candidate chemotherapeutic agent demonstrates effectiveness where the second (post-treatment) levels p27 are increased to a statistically significant degree over the pre-treatment and/or control levels.

In another embodiment, the invention provides a method of determining the effectiveness of a chemotherapeutic agent by further determining, in the isolated sample, a first level of a second surrogate endpoint biomarker such as Ki-67 and/or p-MAPK. After the chemotherapeutic agent has been administered, a second level of Ki-67 and/or p-MAPK is taken and compared to the first (pre-treatment) level and/or a control. The candidate chemotherapeutic agent demonstrates effectiveness where the second (post-treatment) levels of Ki-67 and/or p-MAPK are decreased to a statistically significant degree below the pre-treatment and/or control levels.

Another embodiment of the invention includes a method of screening for pancreatic ductal carcinoma, or a stage of pancreatic cancer in a subject by determining, such as in an isolated sample, the level of a biomarker; namely, p27. The level of the biomarker is then compared to a corresponding control level in one or more control samples. In a preferred embodiment the control samples are obtained from individuals who have been determined not to have pancreatic ductal carcinoma, or a stage of pancreatic cancer.

The determination of a statistically significant increase between the level of the biomarker in the subject and the level of the biomarker in the control sample(s) is indicative of the lack of pancreatic ductal carcinoma, or a stage of pancreatic cancer in the subject. A statistically significant decrease in the level of p27 in the subject, compared to the level of the biomarker in the control sample(s), indicates the presence of pancreatic ductal carcinoma, or a stage of pancreatic cancer in the subject.

In an alternate embodiment, the level of a second biomarker, namely Ki-67 and/or p-MAPK, is determined and compared to a control level of Ki-67 and/or p-MAPK in one or more control samples. A statistically significant increase between the level of Ki-67 and/or p-MAPK in the subject and the control sample(s) is indicative of pancreatic ductal carcinoma, or a stage of pancreatic cancer in the subject. A statistically significant decrease in the level of Ki-67 and/or p-MAPK in the subject, compared to the control sample(s), is indicative of the lack of pancreatic ductal carcinoma, or a stage of pancreatic cancer in the subject.

Methods of determining the level of the biomarker in the subject and control sample(s) are known to the ordinary practitioner. In one embodiment, as an example, the level of the biomarker is determined utilizing an antibody which binds the biomarker. The sample containing the biomarker is contacted with the antibody under conditions which allow binding of the biomarker to the antibody; the presence of the biomarker can then be quantified.

The invention also includes compositions useful in performing the associated methods. For example, the invention includes a composition comprising a plurality of isolated proteins which bind selectively to the protein products of the associated biomarkers; namely, Ki-67 and/or p-MAPK, and p27. In a preferred embodiment, the isolated proteins selectively amplify complementary double stranded DNA. A composition is also included comprising a plurality of biomarker specific primers, wherein each biomarker specific primer selectively amplifies double stranded DNA complementary to a unique biomarker such as Ki-67, p-MAPK and p27. Alternatively, the invention includes a composition comprising a plurality of isolated proteins which bind selectively to the protein products of at least two unique biomarkers, wherein each unique biomarker is selected from the group consisting of Ki-67, p-MAPK and p27.

Methods of determining the levels (e.g. quantifying) of the biomarkers will be readily known to one of ordinary skill and include, but are not limited to, determining expression level, level of RNA, level of RNA product, protein level, and/or protein activity level.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a pancreatic treatment composition and method of pancreatic treatment, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treating pancreatic cancer, comprising administering to a subject in need thereof a therapeutically effective amount of at least one tocotrienol, wherein the tocotrienol is delta-tocotrienol and at least one chemotherapeutic agent, wherein the chemotherapeutic agent is 5-Fluorouracil.

2. The method of claim 1, wherein the composition comprising a therapeutically effective amount of the tocotrienol is administered as a pharmaceutical composition.

3. The method of claim 1, wherein the composition is free of alpha-tocotrienol and beta-tocotrienol.

4. The method of claim 1, wherein the composition is free of at least one tocotrienol selected from the group consisting of alpha-tocotrienol and beta-tocotrienol.

5. The method of claim 1, wherein the composition is free of tocopherols.

6. The method of claim 1, wherein the composition comprises between about 100 mg to 300 mg of the at least one tocotrienol.

7. The method of claim 1, wherein the pancreatic cancer is pancreatic ductal carcinoma.

8. The method of claim 1, wherein the subject is a human.

9. The method of claim 1, wherein the delta-tocotrienol is administered at between 20 µM and 100 µM.

10. The method of claim 9, wherein the delta-tocotrienol is administered at between 40 µM and 100 µM.

11. The method of claim 9, wherein the delta-tocotrienol is administered at 50 µM.

12. The method of claim 1, wherein the 5-Fluorouracil is administered at between 20 µM and 100 µM.

13. The method of claim 12, wherein the 5-Fluorouracil is administered at between 40 µM and 100 µM.

14. The method of claim 12, wherein the 5-Fluorouracil is administered at 50 µM.

* * * * *